(12) United States Patent
Sugiyama

(10) Patent No.: US 11,896,396 B2
(45) Date of Patent: Feb. 13, 2024

(54) SENSOR-EQUIPPED SEAT

(71) Applicant: TS TECH CO., LTD., Saitama (JP)

(72) Inventor: Shinji Sugiyama, Tochigi (JP)

(73) Assignee: TS TECH CO., LTD., Saitama (JP)

( * ) Notice: Subject to any disclaimer, the term of this patent is extended or adjusted under 35 U.S.C. 154(b) by 453 days.

(21) Appl. No.: 17/270,526

(22) PCT Filed: Aug. 14, 2019

(86) PCT No.: PCT/JP2019/031965
§ 371 (c)(1),
(2) Date: Feb. 23, 2021

(87) PCT Pub. No.: WO2020/040018
PCT Pub. Date: Feb. 27, 2020

(65) Prior Publication Data
US 2021/0330264 A1 Oct. 28, 2021

(30) Foreign Application Priority Data
Aug. 24, 2018 (JP) .................. 2018-157506

(51) Int. Cl.
*A47C 7/74* (2006.01)
*A61B 5/02* (2006.01)
(Continued)

(52) U.S. Cl.
CPC ............ *A61B 5/6891* (2013.01); *A47C 7/748* (2013.01); *A61B 5/08* (2013.01); *B60N 2/56* (2013.01);
(Continued)

(58) Field of Classification Search
CPC ......... A47C 7/748; A61B 5/0205; A61B 5/08; A61B 5/6891; A61B 5/6893
See application file for complete search history.

(56) References Cited

U.S. PATENT DOCUMENTS 6,547,728 B1 * 4/2003 Cornuejols .......... G04G 21/025
600/545
8,144,001 B1 * 3/2012 D'Souza .............. A47C 31/105
340/573.1
(Continued)

FOREIGN PATENT DOCUMENTS

JP H04-272705 A 9/1992
JP H09-154835 A 6/1997
(Continued)

OTHER PUBLICATIONS

International Search Report dated Oct. 21, 2019 for the corresponding PCT Application No. PCT/JP2019/031965, with English machine translation.
(Continued)

*Primary Examiner* — Rodney B White
(74) *Attorney, Agent, or Firm* — Michael Best & Friedrich LLP

(57) ABSTRACT

A sensor-equipped seat detecting various parameters and determining a change in physical condition of a seated occupant includes: a surface temperature sensor detecting a seat surface temperature on a seated occupant side and acquiring surface temperature data; an outside air temperature sensor detecting the seat body outside temperature and acquiring outside air temperature data; and a controller having a calculation unit calculating the degree of change in temperature difference from the surface temperature data and the outside air temperature data and a wakefulness determination unit determining a wakefulness state of the seated occupant based on the degree of change. The calculation unit calculates the degree of change in temperature difference from the seat surface temperature in the surface temperature data and the outside air temperature in the outside air temperature data, the degree of data. The wake-
(Continued)

fulness determination unit determines the wakefulness state of the seated occupant based on the degree of change.

9 Claims, 22 Drawing Sheets

(51) Int. Cl.
    *A61B 5/08* (2006.01)
    *A61B 5/00* (2006.01)
    *B60N 2/90* (2018.01)
    *B60N 2/56* (2006.01)
    *A61B 5/0205* (2006.01)

(52) U.S. Cl.
    CPC .............. *B60N 2/90* (2018.02); *A61B 5/0205* (2013.01); *A61B 5/6893* (2013.01); *B60N 2002/981* (2018.02)

(56) References Cited

U.S. PATENT DOCUMENTS

| | | | | |
|---|---|---|---|---|
| 8,598,721 B2* | 12/2013 | Baarman | ................. | A47C 7/72 290/1 R |
| 10,004,873 B1* | 6/2018 | Hur | ........................ | G08B 21/06 |
| 10,433,646 B1* | 10/2019 | Schmidt | ................. | A47C 1/143 |
| 10,562,412 B1* | 2/2020 | Main | .................... | A61B 5/0205 |
| 11,617,451 B1* | 4/2023 | Caruso | ..................... | A47C 7/74 297/217.3 |
| 2002/0183667 A1* | 12/2002 | Kitadou | ............... | A47C 21/006 601/91 |
| 2008/0132383 A1* | 6/2008 | Einav | ................. | A61H 23/0263 482/8 |
| 2008/0269629 A1* | 10/2008 | Reiner | .................. | A61M 21/02 600/544 |
| 2010/0066132 A1* | 3/2010 | Tal Marchand | ......... | A47C 7/68 297/170 |
| 2011/0010014 A1* | 1/2011 | Oexman | .................. | F24F 11/63 600/301 |
| 2011/0015495 A1* | 1/2011 | Dothie | ................. | A47C 31/123 600/300 |
| 2011/0105277 A1* | 5/2011 | Shauli | ................ | A63B 21/1609 482/4 |
| 2013/0226408 A1* | 8/2013 | Fung | ....................... | G08G 1/166 701/1 |
| 2015/0327803 A1* | 11/2015 | Fujita | ....................... | A61B 5/18 340/576 |
| 2016/0089059 A1* | 3/2016 | Hu | ........................ | A61B 5/7207 600/595 |
| 2016/0200220 A1* | 7/2016 | Sugiyama | ................ | A61B 5/18 297/217.2 |
| 2016/0374606 A1* | 12/2016 | Shikii | ................... | A61B 5/4005 600/301 |
| 2018/0118071 A1* | 5/2018 | Sugiyama | ................ | A47C 7/72 |
| 2018/0325270 A1* | 11/2018 | Purser | .................. | A47C 20/041 |
| 2018/0348759 A1* | 12/2018 | Freeman | .............. | A61N 1/3904 |
| 2019/0053748 A1 | 2/2019 | Sugiyama | | |
| 2019/0059589 A1* | 2/2019 | Zhang | .................... | A47C 17/16 |
| 2020/0077800 A1* | 3/2020 | Schmidt | ................. | A47C 1/143 |
| 2020/0383580 A1* | 12/2020 | Shouldice | ............. | B60W 50/14 |
| 2022/0167754 A1* | 6/2022 | Fukuyama | ............. | A61G 7/015 |
| 2022/0167755 A1* | 6/2022 | Fukuyama | ............. | A47C 27/10 |
| 2023/0016979 A1* | 1/2023 | Shimomura | .......... | A61M 21/00 |
| 2023/0137120 A1* | 5/2023 | Kubota | ................ | A47C 20/041 5/616 |

FOREIGN PATENT DOCUMENTS

| | | |
|---|---|---|
| JP | 2005-075198 A | 3/2005 |
| JP | 2005-160495 A | 6/2005 |
| JP | 2005-206011 A | 8/2005 |
| JP | 2013-147225 A | 8/2013 |
| JP | 2017-080297 A | 5/2017 |
| JP | 2018-108765 A | 7/2018 |

OTHER PUBLICATIONS

Japanese Office Action dated Jun. 13, 2023 from the Japan Patent Office (JPO) for the related Japanese Patent Application No. 2020-538336, with machine English translation.

\* cited by examiner

SENSOR-EQUIPPED SEAT

CROSS-REFERENCE TO RELATED APPLICATIONS

This application is entering into the national phase of PCT Application No. PCT/JP2019/031965, filed on Aug. 14, 2019. Further, this application claims the benefit of priority from Japanese Application Number 2018-157506, filed on Aug. 24, 2018, the entire contents of which are incorporated herein by reference.

TECHNICAL FIELD

The present invention relates to a sensor-equipped seat and, more particularly, to a sensor-equipped seat capable of determining a wakefulness state of a seated occupant in a seat.

BACKGROUND ART

In the related art, various seats capable of detecting various types of parameters indicating the state of a seated occupant (driver) and determining a change in physical condition have been proposed so that the seated occupant in a work chair can study or work efficiently and, in the event of a change in the driver's physical condition, the driver in the vehicle seat can be promptly informed of the change (see, for example, PATENT LITERATURES 1 and 2).

The work chair disclosed and described in PATENT LITERATURE 1 has body temperature detecting means for detecting a seated occupant's body temperature. A change in physical condition is determined on the basis of information obtained by the body temperature detecting means, and then the temperature, direction, and volume of windblown out of a blower on a work desk are controlled.

With the above configuration, it is possible to provide a comfortable work space for a seated occupant working at the desk.

The vehicle seat device disclosed and described in PATENT LITERATURE 2 includes temperature measuring means for measuring the temperature of a seated driver's lower limbs, determining means for determining the blood flow inhibition status of the driver's lower limbs on the basis of the rate of change in the temperature measured by the temperature measuring means, and seat driving means for changing the seated occupant's posture so as to alleviate the blood flow inhibition.

With the above configuration, it is possible to provide a comfortable posture in response to the situation of the driver's inhibited blood flow and reduce seating fatigue.

CITATION LIST

Patent Literature

PATENT LITERATURE 1: JP 4-272705 A
PATENT LITERATURE 2: JP 2005-160495 A

SUMMARY OF INVENTION

Technical Problem

By the way, although the seats in PATENT LITERATURES 1 and 2 include detecting means for detecting a seated occupant's body temperature, the seats do not include means for detecting a plurality of parameters of various types including the seated occupant's body temperature.

Accordingly, there has been a demand for a seat capable of detecting a plurality of parameters and determining a change in physical condition of a seated occupant by using the plurality of parameters.

In addition, there has been a demand for a sensor-equipped seat in which the detection accuracy of a detection sensor detecting various types of parameters is improved.

In addition, there has been a demand for a sensor-equipped seat in which a detection sensor and a controller connected to the detection sensor are disposed in a compact manner.

The present invention has been made in view of the above problems, and an object of the present invention is to provide a sensor-equipped seat that detects a plurality of parameters of various types, including a state of a seated occupant, and can determine a change in physical condition of the seated occupant by using the parameters.

In addition, another object of the present invention is to provide a sensor-equipped seat in which the detection accuracy of a detection sensor detecting various types of parameters is improved.

In addition, another object of the present invention is to provide a sensor-equipped seat in which a detection sensor and a controller connected to the detection sensor are disposed in a compact manner.

Solution to Problem

The problems are solved by means of the sensor-equipped seat of the present invention including: a surface temperature sensor detecting a seat surface temperature on a seated occupant side in a seat body and acquiring surface temperature data; an outside air temperature sensor detecting a temperature outside the seat body and acquiring outside air temperature data; and a controller having a calculation unit calculating the surface temperature data and the outside air temperature data and a determination unit determining a change in physical condition of the seated occupant on the basis of information calculated by the calculation unit.

With the above configuration, it is possible to realize a sensor-equipped seat that detects a plurality of parameters of various types, including a state of a seated occupant, and can determine a change in physical condition of the seated occupant by using the parameters.

Specifically, with the sensor-equipped seat, the outside air temperature and the seated occupant-side seat surface temperature related to the body temperature of the seated occupant can be detected and it is possible to determine a change in physical condition of the seated occupant on the basis of the information obtained by calculating the parameters.

It should be noted that means for informing the seated occupant of a change in physical condition of the seated occupant may be provided in the seat body or may be provided in a place other than the seat body.

At this time, the calculation unit may calculate, by computation, a degree of change in temperature difference from the seat surface temperature in the surface temperature data and the outside air temperature in the outside air temperature data, the degree of change in temperature difference being a degree of change per unit time, and the determination unit may be a wakefulness determination unit determining a wakefulness state of the seated occupant on the basis of the degree of change in temperature difference calculated by the calculation unit.

With the above configuration, it is possible to realize a sensor-equipped seat capable of determining the wakefulness state as a change in physical condition of the seated occupant.

At this time, the seat body may be provided with a seating portion supporting the seated occupant from below, and the surface temperature sensor may be attached to the seating portion.

With the above configuration, the seated occupant is less likely to separate from the sensor than in a case where the sensor is attached to the backrest portion or the head portion of the seat, and thus the detection accuracy of the sensor can be improved.

At this time, the surface temperature sensor may be attached at a part behind a middle portion of the seating portion in a front to back direction of the seat.

With the above configuration, it is possible to accurately detect the seated occupant-side seat surface temperature related to the body temperature of the seated occupant. This is because the rear part of the seating portion, which is a position corresponding to the ischial tuberosity of the seated occupant, is apart where a large load is applied by the seated occupant.

At this time, the seating portion may have a pad formed of a cushion material, the surface temperature sensor may be provided on a surface side of the pad, the controller may be provided on a back surface side of the pad, and a harness connecting the surface temperature sensor and the controller through a through hole formed in the pad may be provided.

With the above configuration, the surface temperature sensor and the controller can be disposed in a compact manner.

At this time, a recess portion recessed in a thickness direction of the pad may be formed at a position different from a position of the through hole in the surface of the pad, and the surface temperature sensor may be disposed in the recess portion.

With the above configuration, the surface temperature sensor can be disposed in a compact manner.

At this time, the sensor-equipped seat may include a respiration sensor attached to the seating portion and having a detection unit detecting a respiratory signal of the seated occupant. The detection unit may have a first detection unit and a second detection unit disposed at different positions in a front to back direction of the seat, and the surface temperature sensor may be disposed between the first detection unit and the second detection unit.

With the above configuration, the surface temperature sensor and the respiration sensor can be disposed in a compact manner.

In addition, it is possible to improve the detection accuracy of a pressure sensor by disposing the pressure sensor at a position corresponding to the ischial tuberosity of the seated occupant.

At this time, the respiration sensor may be provided on the surface side of the pad, and a second harness connecting the respiration sensor and the controller through the through hole formed in the pad may be provided.

With the above configuration, a through hole for passing a harness (first harness) is used, and thus a compact disposition can be realized.

At this time, the respiration sensor may detect the respiratory signal of the seated occupant and acquire respiratory data fluctuating with respiration, the controller may further have a second calculation unit calculating, by computation, a degree of change in respiration, the degree of change in respiration being a degree of change in the respiratory data per unit time, and the wakefulness determination unit may determine the wakefulness state of the seated occupant by using a Bayesian filter in which a probability of the seated occupant's drowsiness with regard to the degree of change in respiration is set as a likelihood and the likelihood is multiplied by a prior probability of drowsiness.

With the above configuration, it is possible to realize a sensor-equipped seat capable of detecting the seated occupant's respiration and body temperature and determining the wakefulness state of the seated occupant by combining the parameters.

At this time, the seating portion may be configured by covering a pad as a cushion material with a skin, a seat heater attached to a back surface side of the skin may be provided between the skin and the pad in the seating portion, and the seat heater may be disposed on a surface of the pad at a position different from a position of the surface temperature sensor.

With the above configuration, the seat heater is attached to the back surface of the skin in advance by sewing or the like, and thus the assembly workability of the seat heater is improved and the number of assembled components can be reduced as compared with, for example, the related art in which a seat heater is placed and attached on a cushion pad surface.

Advantageous Effects of Invention

According to the present invention, it is possible to realize a sensor-equipped seat in which the outside air temperature and the seated occupant-side seat surface temperature related to the body temperature of the seated occupant are detected and it is possible to determine a change in physical condition of the seated occupant on the basis of the information obtained by means of the parameters.

In addition, according to the invention, it is possible to realize a sensor-equipped seat capable of determining the wakefulness state as a change in physical condition of the seated occupant.

In addition, according to the invention, the detection accuracy of various sensors can be improved.

In addition, according to the invention, various sensors, a controller, and a harness can be disposed in a compact manner.

In addition, according to the invention, it is possible to realize a sensor-equipped seat capable of detecting the seated occupant's respiration and body temperature and determining the wakefulness state of the seated occupant by combining the parameters.

In addition, according to the invention, the assembly workability of the seat heater is improved and the number of assembled components can be reduced as compared with the related art.

DESCRIPTION OF EMBODIMENTS

Hereinafter, the sensor-equipped seats according to embodiments of the present invention will be described with reference to FIGS. 1 to 22.

The present embodiment relates to the invention of a sensor-equipped seat including a surface temperature sensor that detects the seated occupant-side seat surface temperature and acquires surface temperature data, an outside air temperature sensor that detects the seat body outside temperature and acquires outside air temperature data, and a controller that has a calculation unit calculating the degree of change in temperature difference from the surface temperature data and the outside air temperature data and a wakefulness determination unit determining a wakefulness state of the seated occupant on the basis of the degree of change in temperature difference.

It should be noted that the side on which the seated occupant sits with respect to the backrest portion of the sensor-equipped seat is the front side of the seat.

Figure 1:
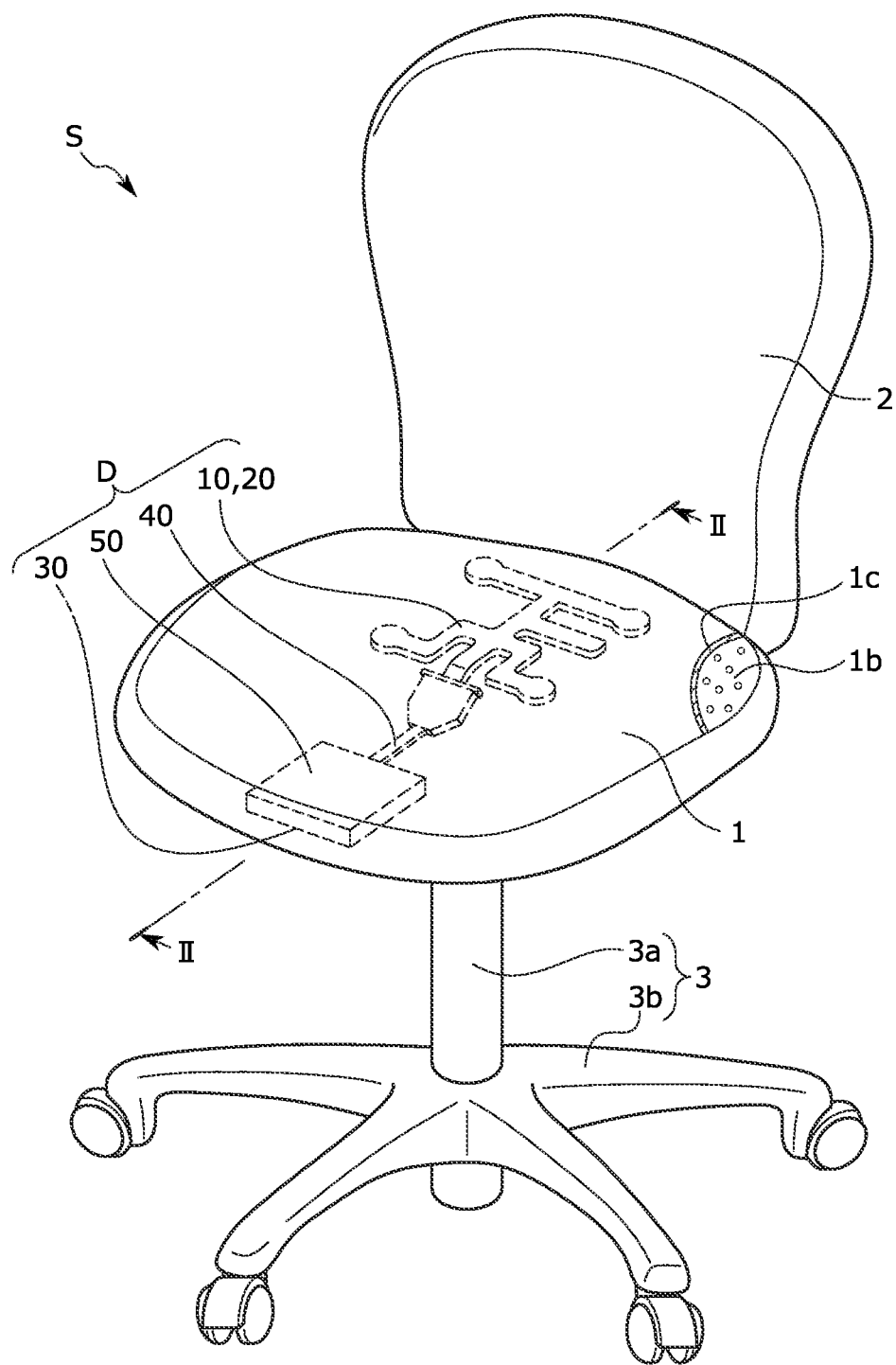
FIG. 1 is an external perspective view of the sensor-equipped seat according to the present embodiment.

A sensor-equipped seat S of the present embodiment is a work chair. As illustrated in FIG. 1, the sensor-equipped seat S mainly includes a seat body having a seating portion 1 and a backrest portion 2, a leg portion 3 supporting the seat body from below, and a wakefulness determination device D attached in the seat body, detecting the seated occupant-side seat surface temperature, the seat body outside temperature, and the respiration of the seated occupant, and determining a wakefulness state of the seated occupant by calculating the parameters.

The wakefulness determination device D mainly includes a surface temperature sensor 10 and a respiration sensor 20 attached to the rear part inside the seating portion 1, an outside air temperature sensor 30 attached to the lower part outside the seating portion 1, and a controller 50 attached to the front part inside the seating portion 1, connected to each of the sensors 10, 20, and 30 through a harness 40, and determining the wakefulness state of the seated occupant by calculating data obtained by each sensor.

Here, the "seat surface temperature" is the temperature of the seat surface fluctuating on the basis of the body temperature of the seated occupant and indicates the body surface temperature of the seated occupant.

Figure 2:
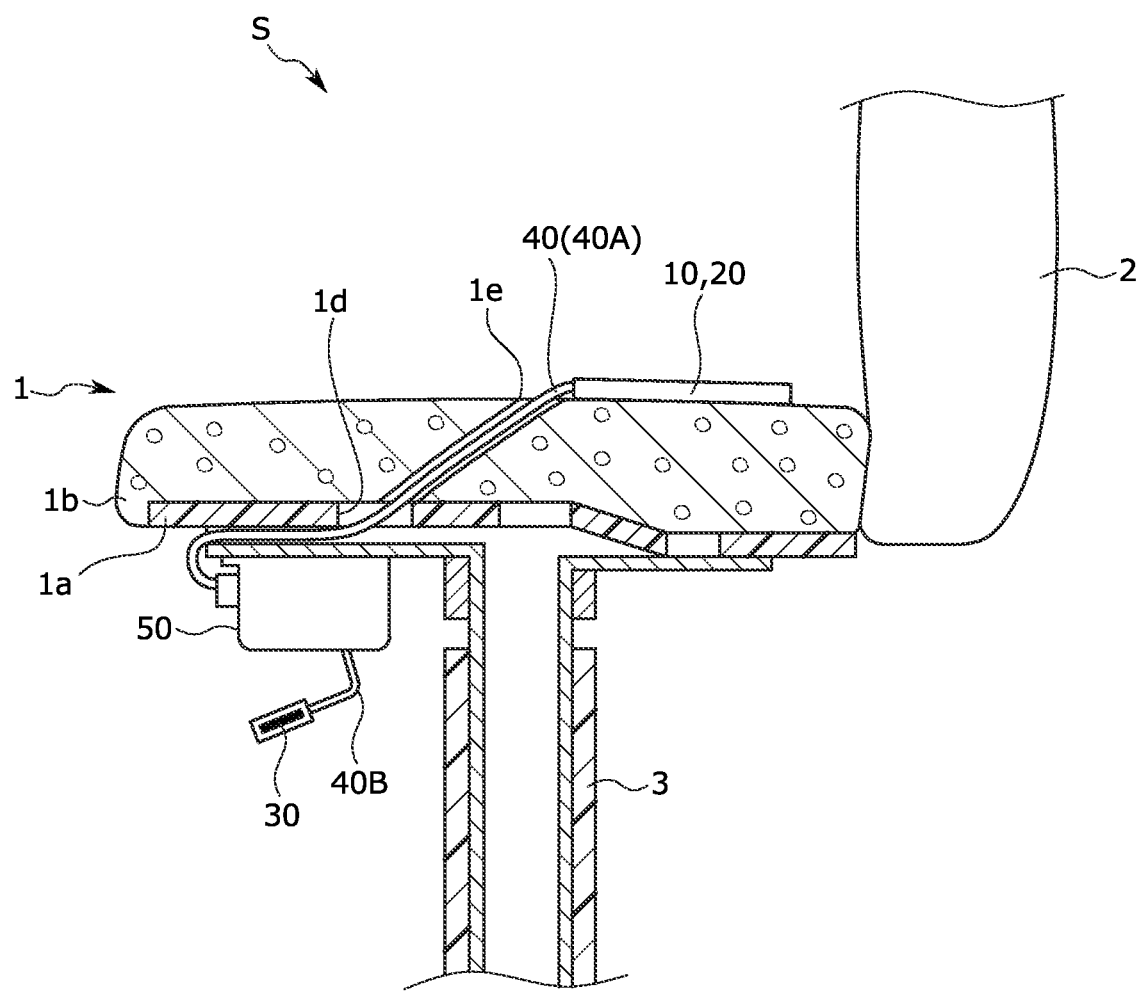
FIG. 2 is a cross-sectional view taken along line II-II of FIG. 1 and illustrates each sensor and a controller.

The seating portion 1 is a cushion pan supporting the buttocks of the seated occupant from below. As illustrated in FIGS. 1 and 2, the seating portion 1 is configured by placing a pad 1b as a cushion material on the upper surface of a seating frame 1a as a skeleton and covering the pad 1b with a skin 1c.

Through holes 1d and 1e for passing the harness 40 connecting the sensors 10 and 20 and the controller 50 are formed in the seating frame 1a and the pad 1b, respectively. The through holes 1d and 1e are disposed so as to communicate with each other in the up to down direction.

The backrest portion 2 is a back pan supporting the back of the seated occupant from behind. The backrest portion 2 is configured by placing a pad (not illustrated) on the front surface of a backrest frame (not illustrated) as a skeleton and covering the pad with a skin (not illustrated).

The leg portion 3 is a resin member supporting the seating portion 1 and the backrest portion 2. As illustrated in FIG. 1, the leg portion 3 includes a leg prop portion 3a attached to the bottom surface of the seating portion 1 and extending in the up to down direction and a leg branching portion 3b attached to the lower end part of the leg prop portion 3a and branching into a plurality of pieces.

Figure 3:
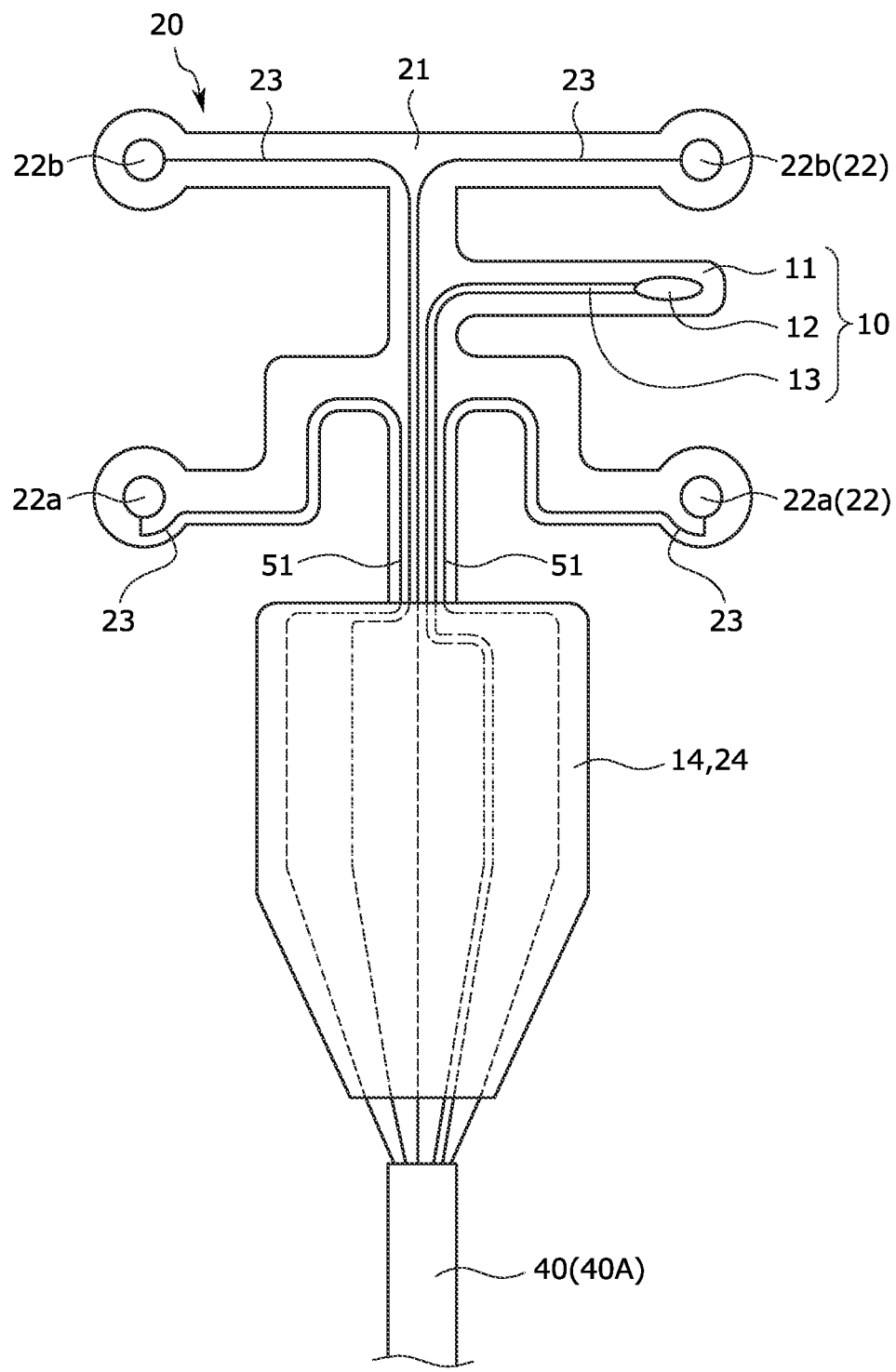
FIG. 3 is a diagram illustrating a surface temperature sensor, a respiration sensor, and a transmission path.

As illustrated in FIGS. 2 and 3, the surface temperature sensor 10 is a thermistor for measuring the seat surface temperature. Specifically, the surface temperature sensor 10 detects the seat surface temperature of the seating portion 1 and acquires surface temperature data fluctuating with the seat surface temperature.

The surface temperature sensor 10 is disposed between the pad 1b and the skin 1c at the rear part of the seating portion 1 and is attached on the surface of the pad 1b by means of an adhesive, double-faced tape, or the like.

As illustrated in FIG. 3, the surface temperature sensor 10 mainly includes a seat base material 11 as a sensor base material, a detection unit 12 provided on the seat base material 11 and detecting the seat surface temperature, a transmission path 13 for transmitting the surface temperature data obtained by the detection unit 12 toward the harness 40, and a connection path 14 for connecting the transmission path 13 and the harness 40.

The connection path 14 is tapered such that the part of connection to the harness 40 is narrower than the part of connection to the transmission path 13.

As illustrated in FIGS. 2 and 3, the respiration sensor 20 is a biological sensor detecting a respiratory signal of the seated occupant. Specifically, the respiration sensor 20 is a planar pressure sensor detecting the seating pressure of the seated occupant.

Here, the "seating pressure" is a value that periodically changes in response to the physiological activity (respiration) of the seated occupant when the seated occupant is seated on the sensor-equipped seat S and is a value detected by the respiration sensor 20.

As in the case of the surface temperature sensor 10, the respiration sensor 20 is disposed between the pad 1b and the skin 1c at the rear part of the seating portion 1 and is attached on the surface of the pad 1b by means of an adhesive, double-faced tape, or the like.

As illustrated in FIG. 3, the respiration sensor 20 mainly includes a substantially H-shaped seat base material 21, four detection units 22 provided on the seat base material 21 and detecting the seat surface temperature, a transmission path 23 for transmitting the surface temperature data obtained by each detection unit 22 toward the harness 40, and a connection path 24 connecting the transmission path 23 and the harness 40.

It should be noted that the surface temperature sensor 10 and the respiration sensor 20 are integrated in the present embodiment and the harness 40 connected to the sensors 10 and is also integrated into one. Accordingly, compact disposition and assembly work simplification can be achieved.

The detection unit 22 has right and left first detection units 22a disposed on the front side of the seat and right and left second detection units 22b disposed behind the right and left first detection units 22a.

The right and left first detection units 22a and the right and left second detection units 22b are provided on the right and left sides, respectively. The right and left first detection units 22a and the right and left second detection units 22b are disposed at positions sandwiching the middle part of the seating portion 1.

Accordingly, the detection units 22a and 22b are disposed at positions where the detection units 22a and 22b easily come into contact with the right and left buttocks (ischial tuberosity) of the seated occupant and the respiratory signal of the seated occupant can be detected more stably.

The surface temperature sensor 10 (detection unit 12) is disposed between the first detection unit 22a and the second detection unit 22b in the front to back direction of the seat. The detection unit 12 is also disposed at a position where the detection unit 12 easily comes into contact with the buttocks (ischial tuberosity) of the seated occupant. Accordingly, the body surface temperature of the seated occupant is measured with ease.

As illustrated in FIG. 2, the outside air temperature sensor 30 is a thermistor for measuring the temperature outside the seat body. Specifically, the outside air temperature sensor 30 detects the seat body outside temperature and acquires outside air temperature data fluctuating with the outside temperature.

The outside air temperature sensor 30 is disposed so as to slightly project downward from the controller 50 at the front part of the seating portion 1.

The outside air temperature sensor 30 includes a seat base material (not illustrated) as a sensor base material and a detection unit (not illustrated) provided on the seat base material and detecting the outside air temperature. The outside air temperature data obtained by the detection unit can be transmitted to the controller 50 through the harness 40.

As illustrated in FIGS. 1 and 2, the harness 40 is a wire harness formed by bundling a plurality of electric wires (transmission paths) in order to electrically connect the sensors 10, 20, and 30 and the controller 50.

The harness 40 is formed by bundling the transmission paths of the surface temperature sensor 10 and the respiration sensor 20 and has a harness 40A connecting the sensors and the controller 50 and a harness 40B connecting the outside air temperature sensor 30 and the controller.

More specifically, the harness 40A extends from the controller 50 to the rear of the seat through a gap (not illustrated) provided in the seating frame 1a, passes through the through holes 1d and 1e, extends above the seat, and is connected to the sensors 10 and 20.

The harness 40B extends from the controller 50 to the lower side of the seat and is connected to the outside air temperature sensor 30.

As illustrated in FIGS. 1 and 2, the controller 50 corresponds to an electronic control unit (ECU) and is a central function that comprehensively executes electrical control.

The controller 50 is configured to determine the wakefulness state of the seated occupant by acquiring the surface temperature data obtained by the surface temperature sensor 10 and the outside air temperature data obtained by the outside air temperature sensor 30. In a case where the controller 50 determines that the seated occupant is not wakeful, the controller 50 transmits a drive signal for driving a drive motor 51a toward a drive unit 51.

It should be noted that the controller 50 is capable of comprehensively determining the wakefulness state of the seated occupant by acquiring the respiratory data obtained by the respiration sensor 20 in addition to the surface temperature data and the outside air temperature data.

Figure 4:
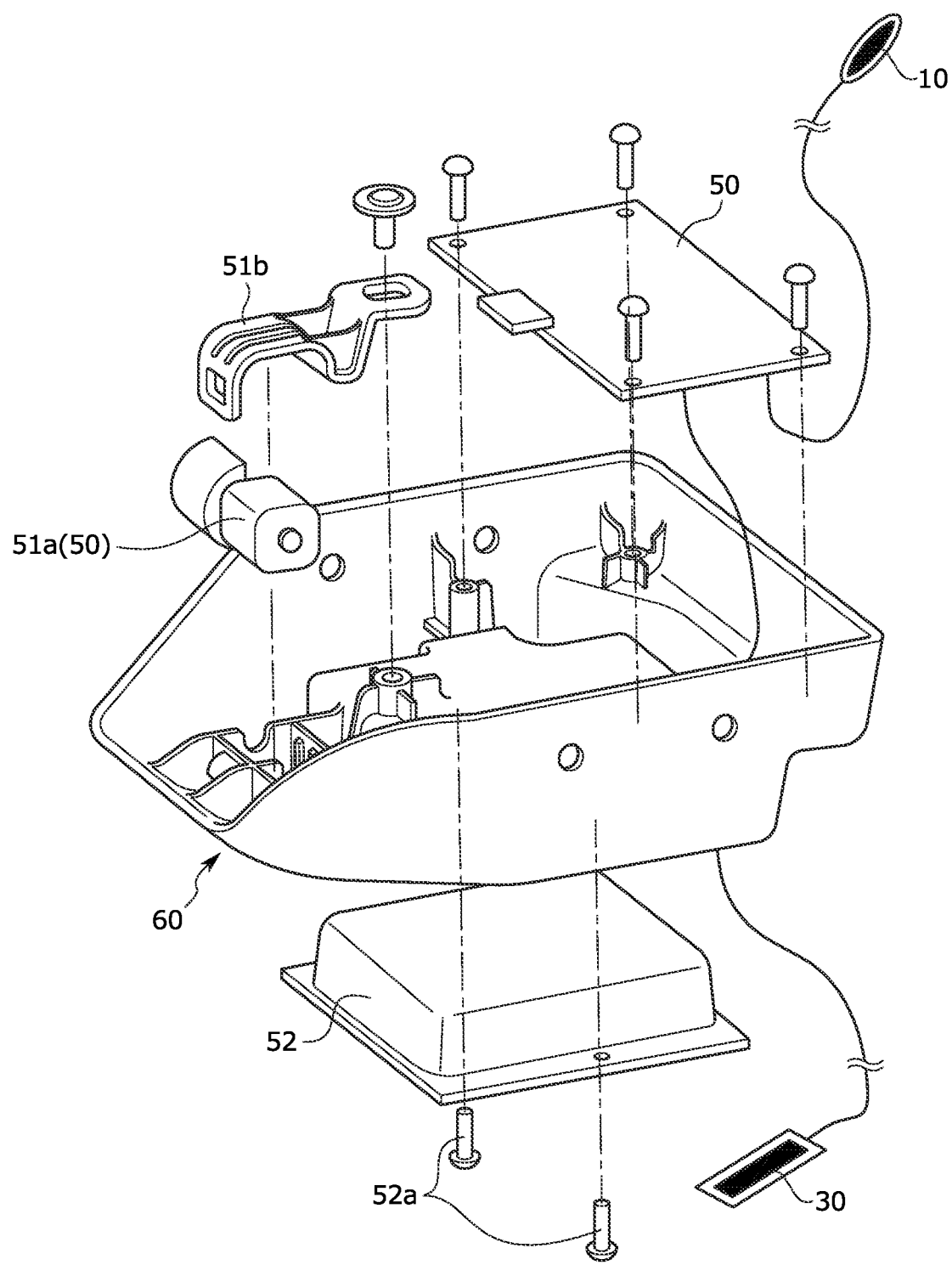
FIG. 4 is an exploded perspective view of a controller unit.

As illustrated in FIG. 4, the controller 50 is stored inside a protective cover 60 together with the drive unit 51 and a battery 52 and the protective cover 60 is attached to the bottom surface of the seating frame 1a at the front part of the seating portion 1.

The drive unit 51 has the drive motor 51a that starts driving by receiving the drive signal from the controller 50 and applies a physical stimulus to the seated occupant by the driving of the drive motor 51a. The drive unit 51 is attached by means of an attachment member 51b.

The battery 52 is a plate-shaped rechargeable battery for supplying electric power to the controller 50, the drive unit 51, and other components and is attached by means of an attachment member 52a.

It should be noted that the protective cover 60 is a housing that has an opening part in the front wall portion thereof and has a shape facilitating the extension of the harness 40.

<Software Configuration of Controller 50>

Figure 5:
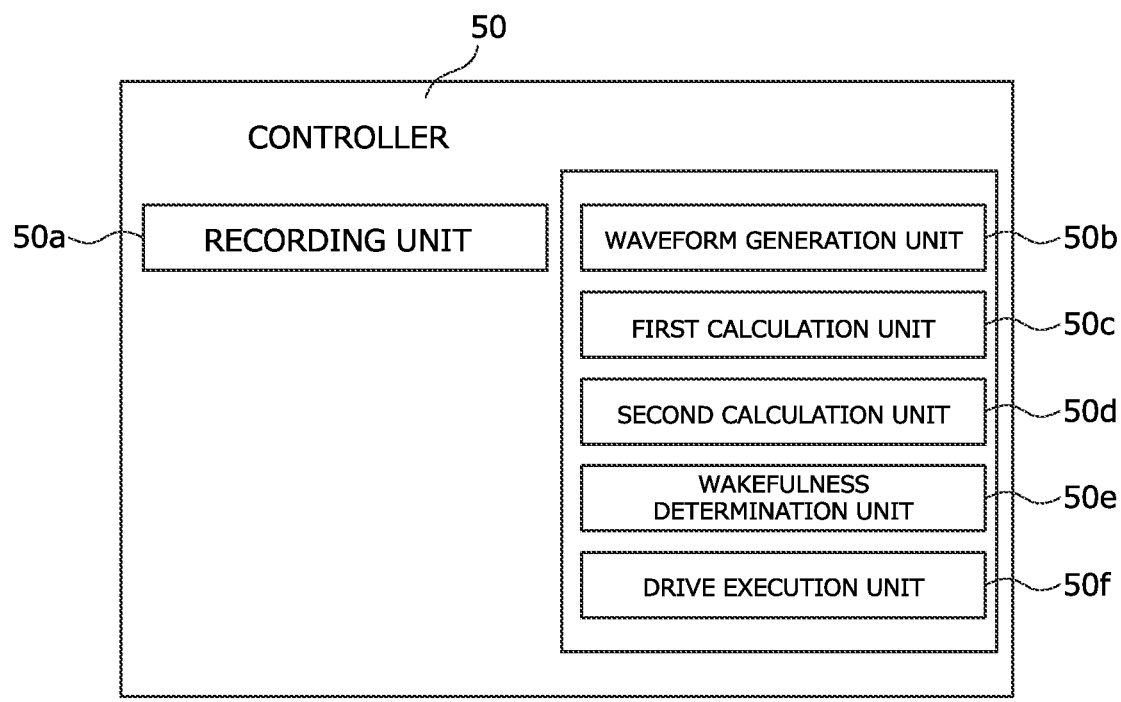
FIG. 5 is a diagram illustrating the software configuration of the controller.

As illustrated in FIG. 5, the controller 50 includes a recording unit 50a configured by a RAM (not illustrated), a waveform generation unit 50b generating voltage waveform data, a first calculation unit 50c and a second calculation unit 50d performing data calculation for wakefulness determination, a wakefulness determination unit 50e performing wakefulness determination, and a drive execution unit 50f driving the drive unit 51.

The software configurations of the controller 50 function by the CPU (not illustrated) of the controller 50 executing a program stored in a ROM (not illustrated).

The recording unit 50a temporarily stores various parameters including signals during arithmetic control and input and output signals. Specifically, the recording unit 50a records, for example, a respiratory signal or a temperature signal converted into a digital signal.

Figure 6:
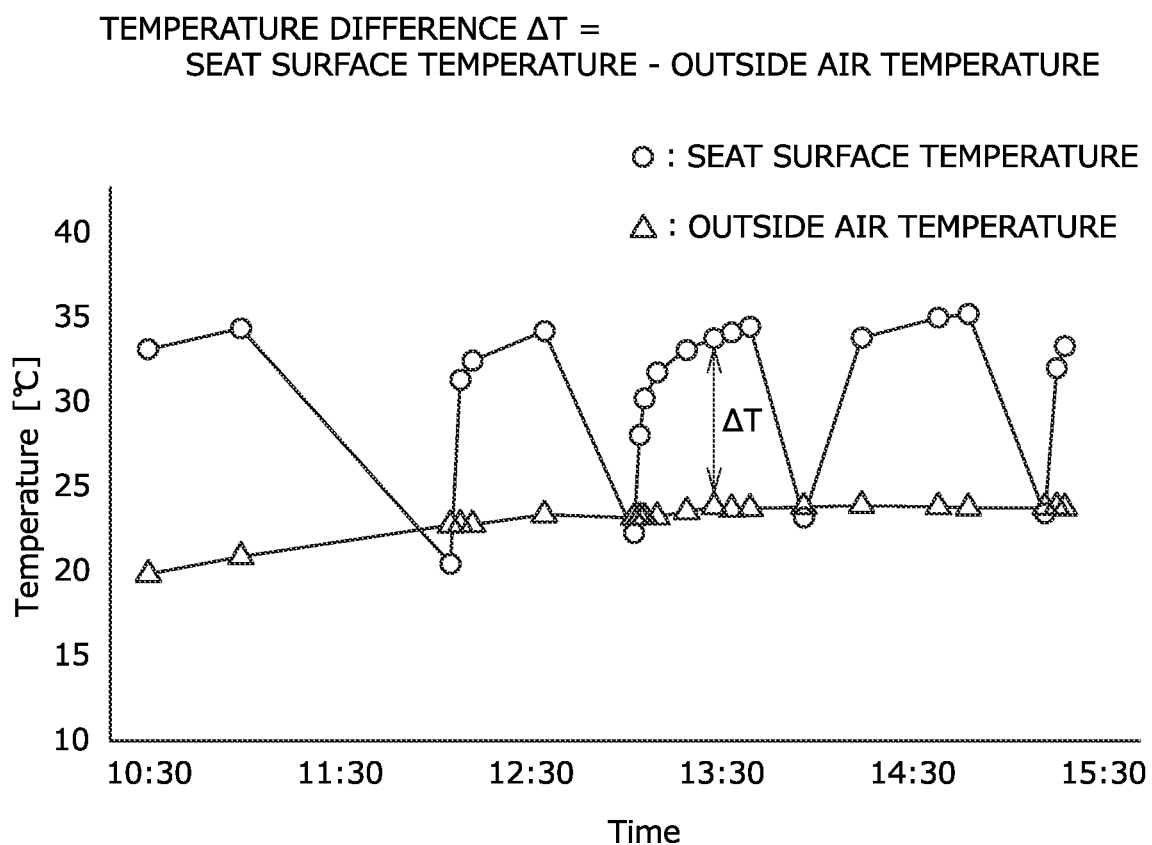
FIG. 6 is a graph of temperature waveform data showing changes over time in seat surface and outside air temperatures.

The waveform generation unit 50b has a function of generating the temperature waveform data shown in FIG. 6, in which the vertical axis represents the surface temperature data and the outside air temperature data obtained from the surface temperature sensor 10 and the outside air temperature sensor 30 and the horizontal axis represents time.

In addition, the waveform generation unit 50b has a function of generating respiratory waveform data (not illustrated) in which the vertical axis represents the respiratory data obtained from the respiration sensor 20 and the horizontal axis represents time.

The first calculation unit 50c calculates, by computation, the degree of change in a temperature difference ΔT, which is a degree of change per unit time, from the seat surface temperature and the outside air temperature on the basis of the temperature waveform data generated by the waveform generation unit 50b and shown in FIG. 6.

The second calculation unit 50d calculates, by computation, the degree of change in respiration, which is the degree of change in the respiratory data per unit time, on the basis of the respiratory waveform data (not illustrated) generated by the waveform generation unit 50b.

The wakefulness determination unit 50e determines the wakefulness state of the seated occupant on the basis of the degree of change in the temperature difference ΔT calculated by the first calculation unit 50c.

Specifically, the wakefulness determination unit 50e determines that the seated occupant is not wakeful (determines that the degree of wakefulness of the seated occupant has decreased) when the temperature difference ΔT is 8.0 degrees or more and 12.0 degrees or less, more preferably 9.0 degrees or more and 11.0 degrees or less, and even more preferably 9.5 degrees or more and 10.5 degrees or less.

In addition, the wakefulness determination unit 50e is capable of determining the wakefulness state of the seated occupant by using a Bayesian filter in which the probability of the seated occupant's drowsiness with regard to the degree of change in respiration is set as a likelihood and the likelihood is multiplied by the prior probability of drowsiness.

It should be noted that a known determination method (such as the determination method described in JP 6114802 B1) can be used as a specific method for determining the wakefulness state on the basis of the degree of change in respiration and specific description is omitted.

The drive execution unit 50f drives the drive unit 51 in response to a determination that the degree of wakefulness of the seated occupant has decreased and applies a vibration stimulus to the seated occupant.

<Wakefulness State Determination Processing>

Next, the wakefulness state determination processing that is executed by the wakefulness determination device D will be described with reference to FIG. 7.

The wakefulness state determination processing according to the present embodiment is to calculate, by computation, the degree of change in the temperature difference ΔT, which is a degree of change per unit time, from the seat surface temperature in the surface temperature data and the outside air temperature in the outside air temperature data and determine the wakefulness state of the seated occupant on the basis of the calculated degree of change in the temperature difference ΔT.

Figure 7:
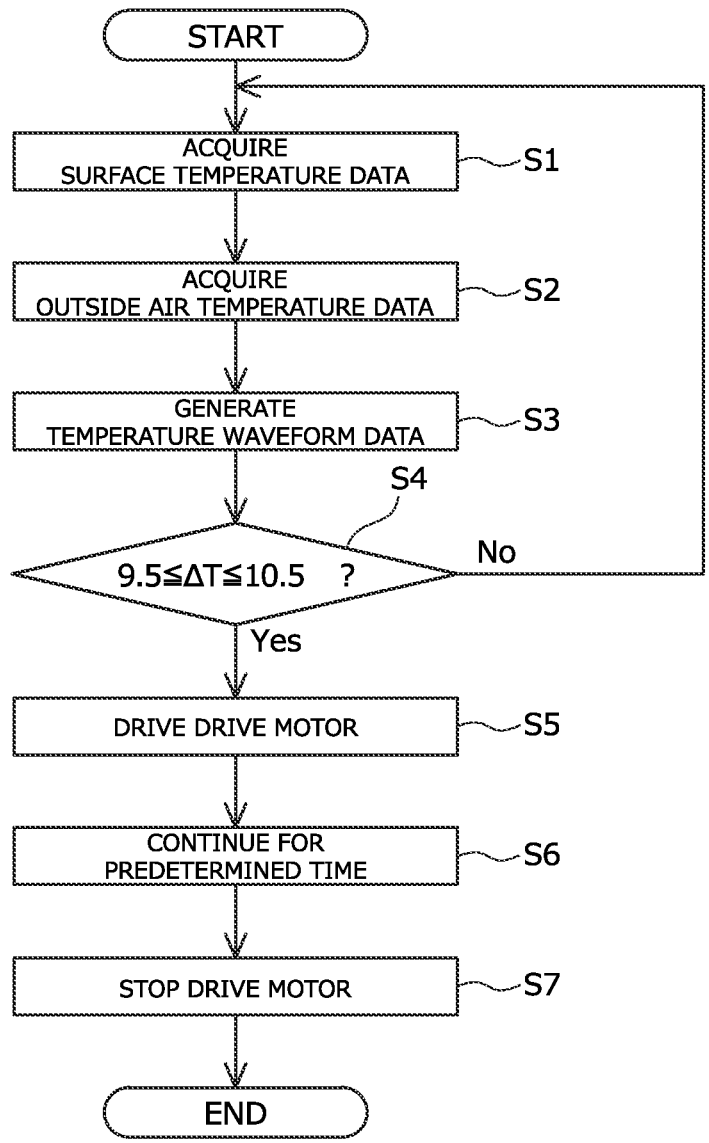
FIG. 7 is a flowchart illustrating an example of wakefulness state determination processing.

In the "wakefulness state determination processing flow" illustrated in FIG. 7, the surface temperature sensor 10 first acquires the surface temperature data fluctuating with the seated occupant-side seat surface temperature by using the pressing of a start switch (not illustrated) as a key (Step S1). Then, the outside air temperature sensor 30 acquires the outside air temperature data fluctuating with the seat body outside temperature (Step S2).

More specifically, the surface temperature sensor 10 and the outside air temperature sensor 30 acquire the surface temperature data and the outside air temperature data as the surface temperature data acquisition step and the outside air temperature acquisition step, respectively. Then, the controller 50 records the surface temperature data and the outside air temperature data transmitted from the sensors 10 and 30 in the recording unit 50a as potential difference data (Steps S1 and S2).

Next, the waveform generation unit 50b generates the temperature waveform data shown in FIG. 6, which is the transition of the surface temperature and the outside air temperature over a predetermined time, on the basis of the acquired surface temperature data and outside air temperature data (Step S3).

Next, the first calculation unit 50c calculates, by computation, the degree of change in the temperature difference ΔT, which is a degree of change per unit time, from the generated temperature waveform data shown in FIG. 6 in the calculation step. Specifically, the average value of the temperature difference ΔT is calculated for each 30-second section.

Then, the wakefulness determination unit 50e determines whether or not the calculated temperature difference ΔT in one section is 9.5 degrees or more and 10.5 degrees or less (Step S4).

When the wakefulness determination unit 50e determines that the temperature difference ΔT is 9.5 degrees or more and 10.5 degrees or less (Step S4: Yes), it is highly possible that the seated occupant is not wakeful. Accordingly, the drive execution unit 50f drives the drive unit 51 to apply a vibration stimulus to the seated occupant (Step S5).

On the other hand, when the wakefulness determination unit 50e determines that the temperature difference ΔT is not 9.5 degrees or more and 10.5 degrees or less (Step S4: No), the processing returns to the surface temperature data acquisition step (Step S1).

Next, the drive execution unit 50f applies a vibration stimulus to the seated occupant for a predetermined time by continuing to drive the drive unit 51 for a predetermined time (Step S6) and then stops the drive unit 51 (Step S7).

With the wakefulness state determination processing described above, it is possible to relatively accurately determine whether or not the seated occupant is wakeful and, when it is determined that the seated occupant is not wakeful (when it is determined that the seated occupant is in a low-wakefulness state), the drive unit 51 can be driven in a timely manner and the wakefulness state of the seated occupant can be efficiently maintained.

<Other Wakefulness State Determination Processing>

Figure 8:
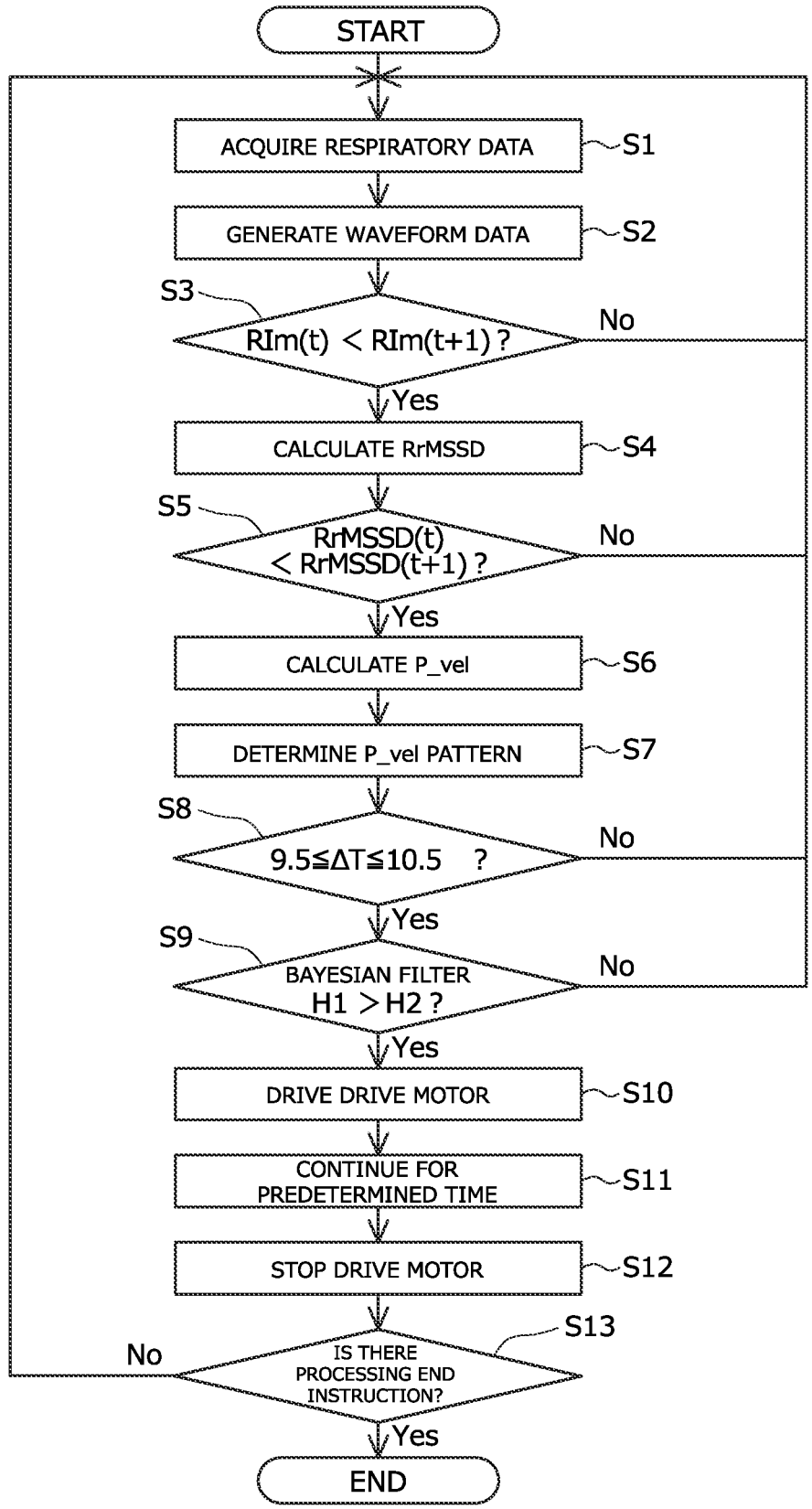
FIG. 8 is a flowchart illustrating an example of wakefulness state determination processing including respiratory data.

In another wakefulness state determination processing, the wakefulness determination device D is capable of comprehensively determining the wakefulness state of the seated occupant by acquiring the respiratory data obtained by the respiration sensor 20 in addition to the surface temperature data and the outside air temperature data as illustrated in FIG. 8.

Specifically, it is possible to determine the wakefulness state of the seated occupant on the basis of the degree of change in the temperature difference ΔT and by means of the Bayesian filter in which the probability of the seated occupant's drowsiness with regard to the degree of change in respiration is set as a likelihood and the likelihood is multiplied by the prior probability of drowsiness.

It should be noted that the "wakefulness state determination processing flow" illustrated in FIG. 8 is an already known determination processing flow (such as the determination processing flow described in JP 6114802 B1) except for Step S8, the processing of Step S8 has already been described above, and thus detailed description thereof is omitted.

With the wakefulness state determination processing described above, it is possible to even more accurately determine whether or not the seated occupant is wakeful and efficiently maintain the wakefulness state of the seated occupant.

Second Embodiment of Sensor-Equipped Seat

Next, a sensor-equipped seat S2 according to the second embodiment will be described with reference to FIG. 9.

It should be noted that the description of content overlapping with the sensor-equipped seat S2 is omitted in the following description.

The sensor-equipped seat S2 is different from the sensor-equipped seat S in that the sensor-equipped seat S2 is configured to include a seat heater 70.

Figure 9:
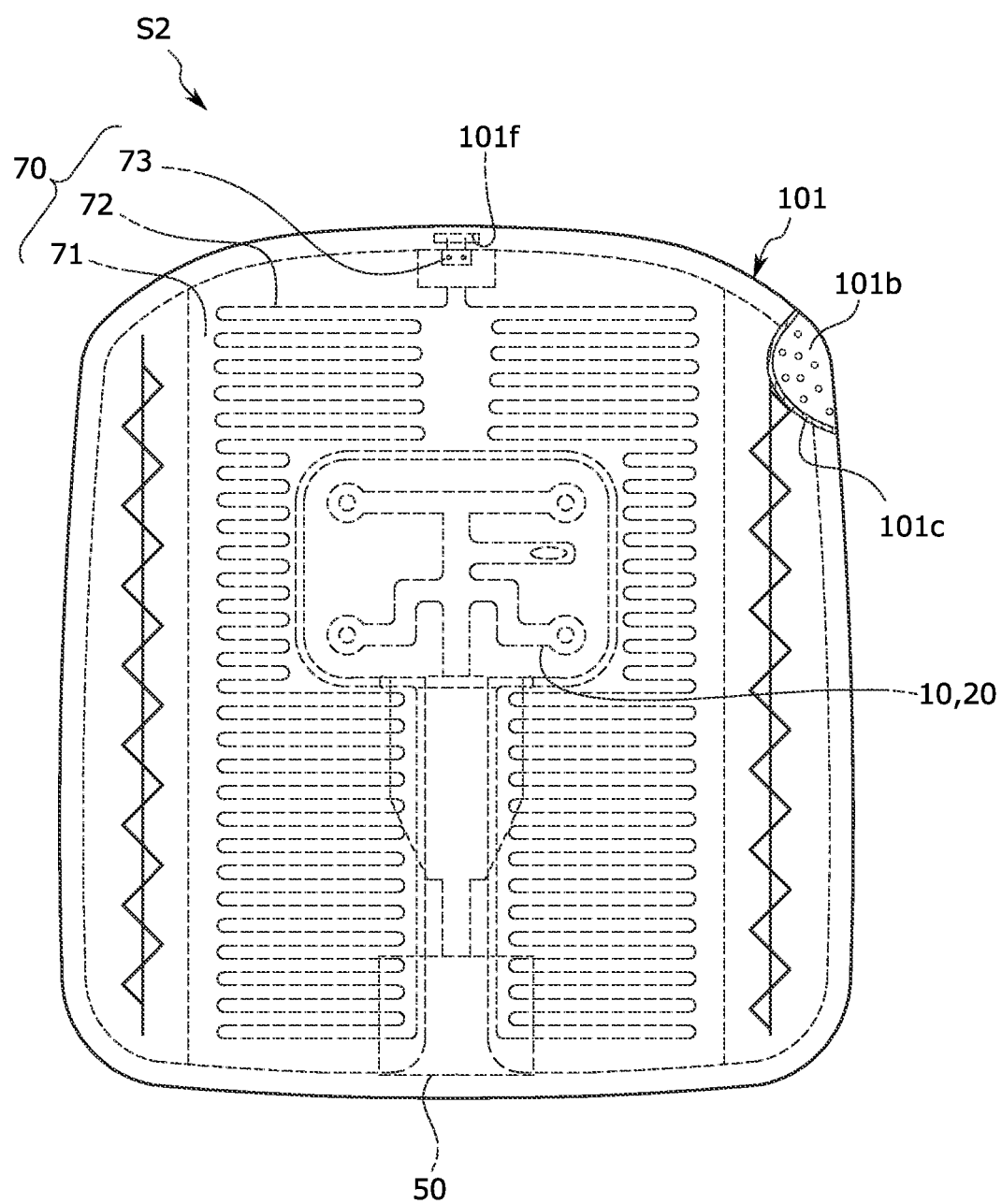
FIG. 9 is a top view of the pad of the sensor-equipped seat of a second embodiment.

As illustrated in FIG. 9, the sensor-equipped seat S2 further includes the seat heater 70 disposed between a pad 101b and a skin 101c in a seating portion 101.

The seat heater 70 is a planar heating element that warms the seating portion 101. The seat heater 70 includes a seat base material 71, a heater wire 72 fixed to the seat base material 71 and extending in a predetermined wavy pattern, and a connector 73 connected to the extending end portion of the heater wire 72 on the seat base material 71.

The connector 73 passes through a through hole 101f provided in the pad 101b and is connected to an electrical system (not illustrated).

As illustrated in FIG. 9, the seat heater 70 is disposed on the surface of the pad 101b at a position different from the positions of the sensors 10 and 20 and the controller 50.

In addition, the right and left side parts of the seat heater 70 are attached by sewing to the back surface of the skin 101c.

With the above configuration, the assembly workability of the seat heater 70 can be improved and the number of assembled components can be reduced as compared with, for example, a case where the seat heater 70 is attached on the surface of the pad 101b. In addition, mutual interference between the seat heater 70 and the sensors 10 and 20 and the controller 50 can be avoided.

Third Embodiment of Sensor-Equipped Seat

Figure 10:
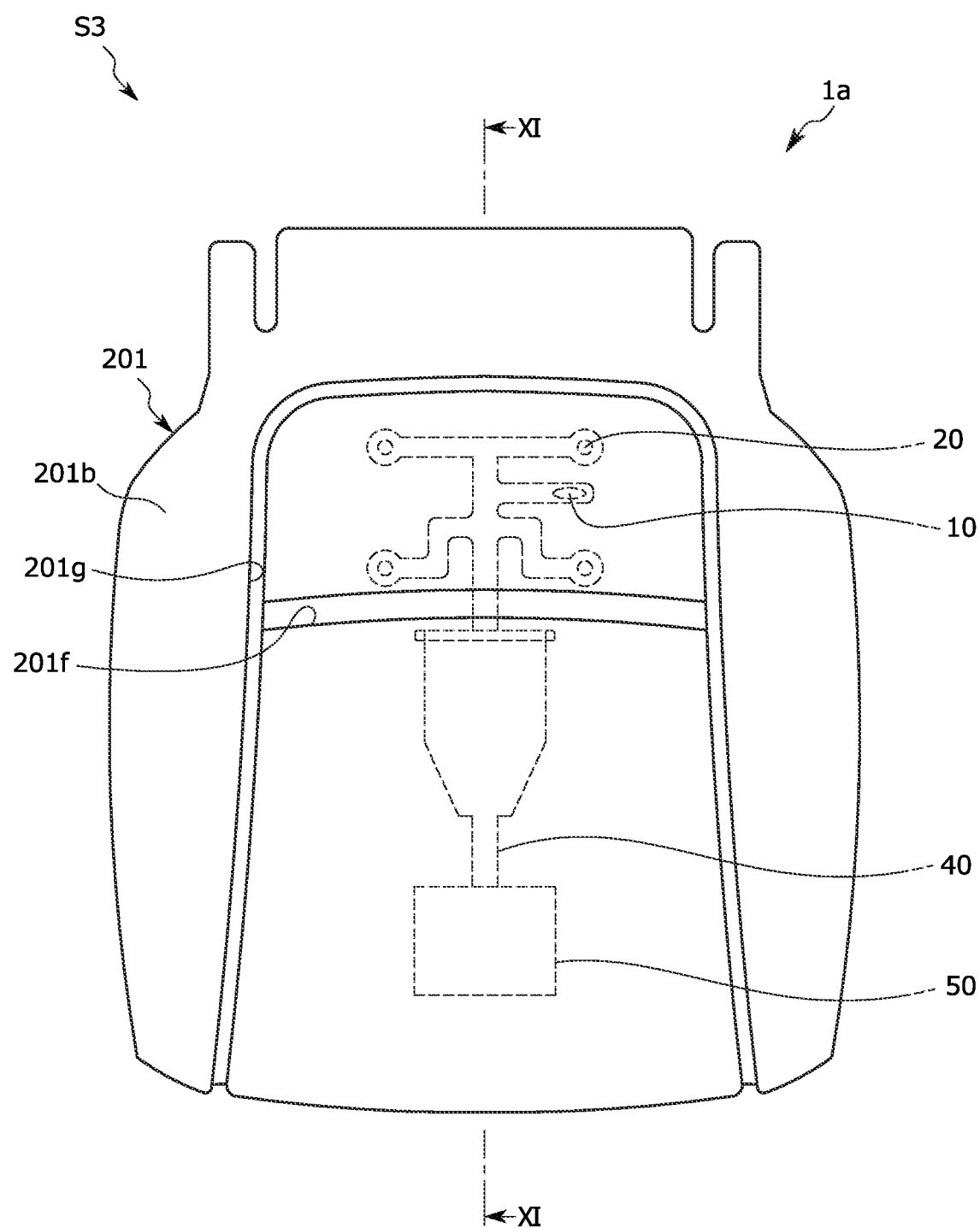
FIG. 10 is a top view of the cushion pad of the sensor-equipped seat of a third embodiment.

Next, a sensor-equipped seat S3 according to the third embodiment will be described with reference to FIGS. 10 and 11.

The sensor-equipped seat S3 is different from the sensor-equipped seat S in that the sensor-equipped seat S3 is a conveyance seat.

The sensor-equipped seat S3 includes a seating portion 201. The seating portion 201 is configured by placing a pad 201b on the upper surface of a seating frame 201a as a skeleton and covering the pad 201b with a skin (not illustrated).

Through holes 201d and 201e for passing the harness 40 connecting the sensors 10 and 20 and the controller 50 are formed in the seating frame 201a and the pad 201b, respectively. The through holes are disposed so as to communicate with each other in the up to down direction.

In addition, a hanging recess portion 201f as a recess portion for hanging a skin end portion (not illustrated) and a substantially U-shaped hanging recess portion 201g provided so as to surround the sensors 10 and 20 are formed on the surface of the pad 201b at a substantially middle part in the front to back direction of the seat.

The hanging recess portion 201f is formed at a position between the harness 40 and the surface temperature and respiration sensors 10 and 20 and in front of the sensors 10 and 20 in the front to back direction of the seat.

Fourth Embodiment of Sensor-Equipped Seat

Figure 12:
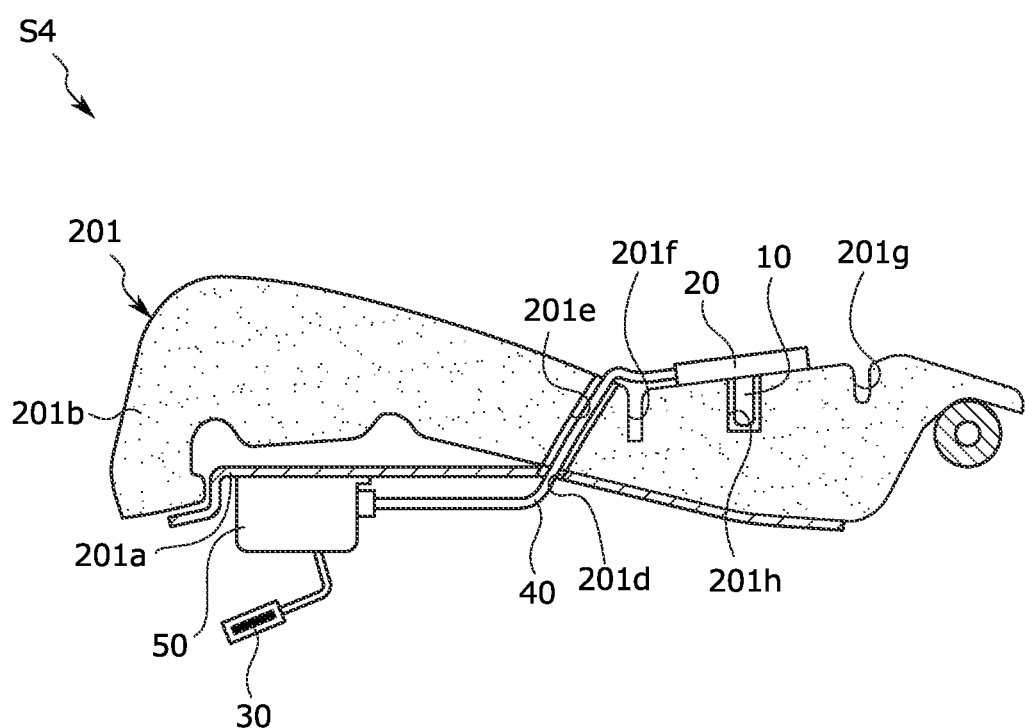
FIG. 12 is a cross-sectional view taken along line XI-XI of the cushion pad of a fourth embodiment.

Next, a sensor-equipped seat S4 according to the fourth embodiment will be described with reference to FIG. 12.

Figure 11:
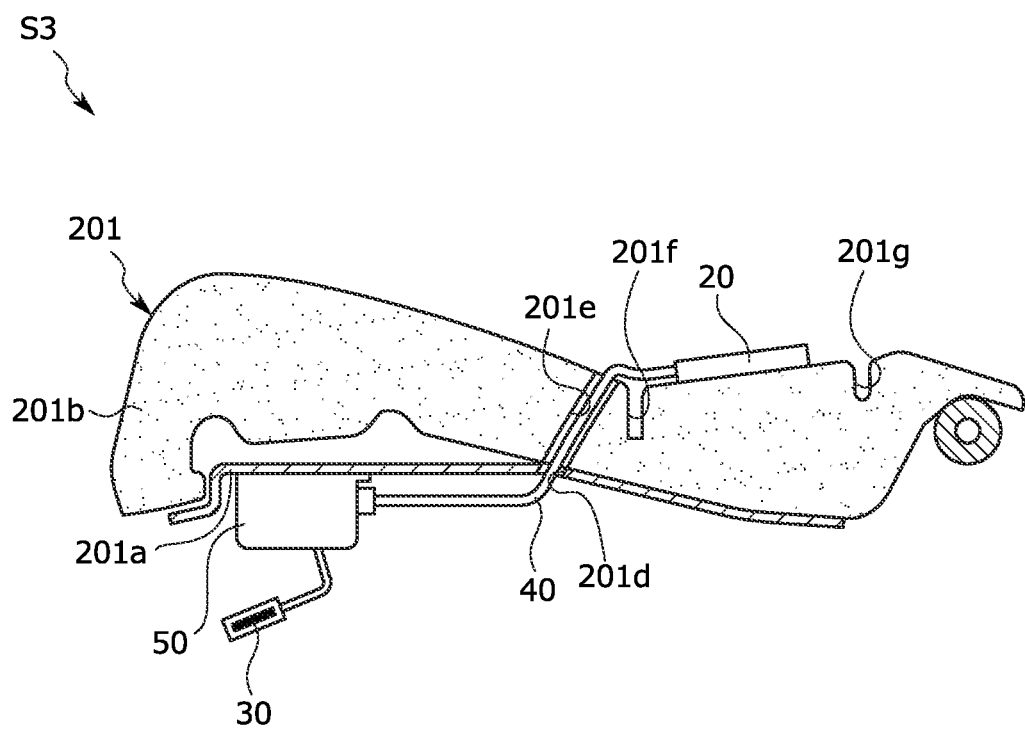
FIG. 11 is a cross-sectional view taken along line XI-XI of the cushion pad of the third embodiment.

In the sensor-equipped seat S4 as compared with the sensor-equipped seat S3 in FIG. 11, the surface temperature sensor 10 is formed at a position facing a hanging recess portion 201h and stored in the hanging recess portion 201f.

The configuration described above realizes a conveyance seat in which the surface temperature sensor 10 is disposed in a compact manner.

<Fifth Embodiment of Sensor-Equipped Seat>
"Equipped with Air Conditioning Blower"

Next, a sensor-equipped seat S5 according to the fifth embodiment will be described with reference to FIGS. 13 to 15.

The sensor-equipped seat S5 is different from the sensor-equipped seat S3 in FIG. 11 mainly in that the sensor-equipped seat S5 is a conveyance seat including a blower device 80 and a duct 90.

The sensor-equipped seat S5 is configured by covering a seat frame as a skeleton with a pad made of urethane foam or the like and a skin made of cloth, leather, or the like. The pad covers the seat frame and the skin covers the pad.

Figure 13:
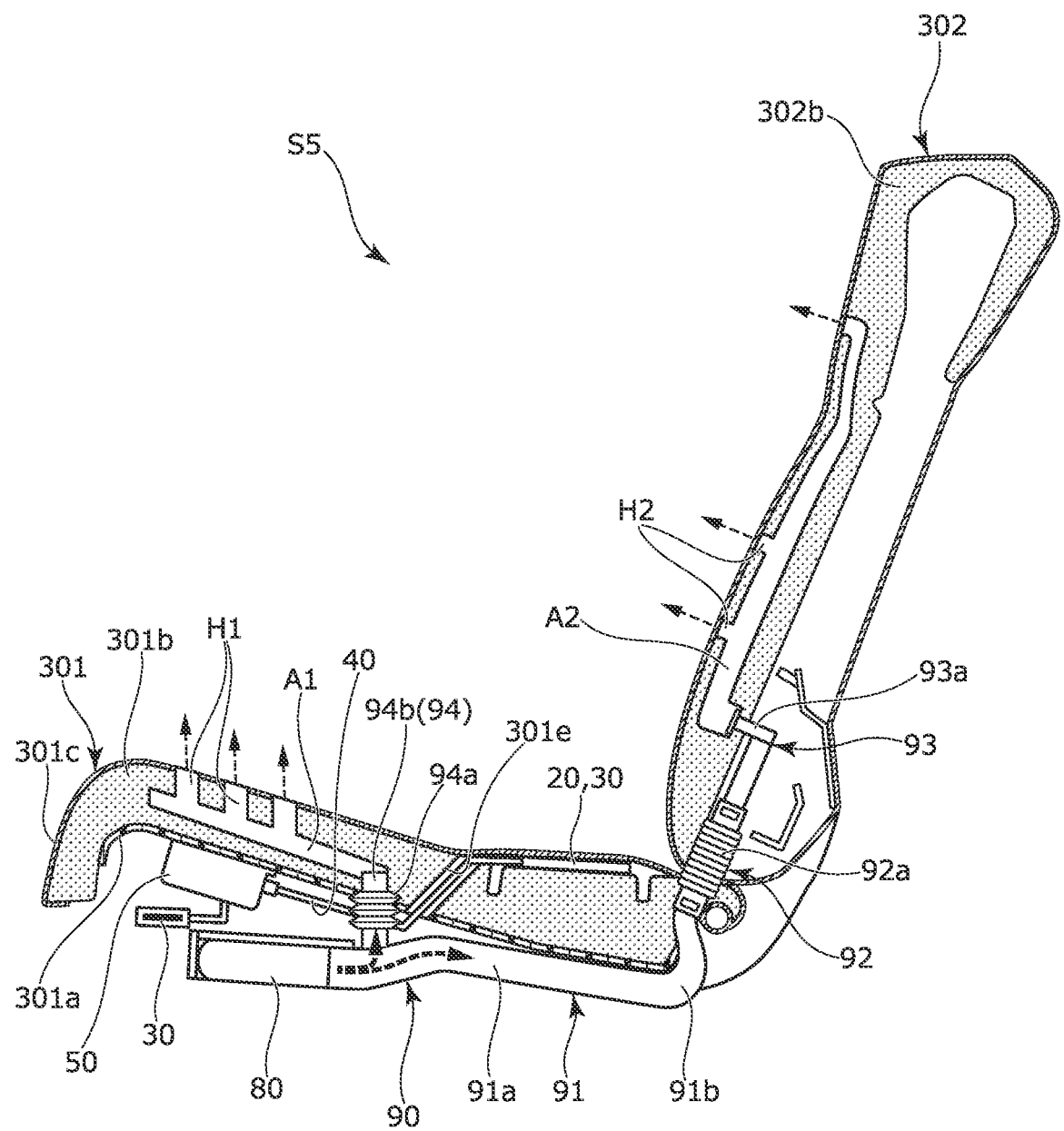
FIG. 13 is a vertical cross-sectional view of the sensor-equipped seat of a fifth embodiment.

As illustrated in FIG. 13, the pad includes a cushion pad 301b constituting the pad of a seating portion 301 and a back pad 302b constituting the pad of a backrest portion 302.

The cushion pad 301b has a ventilation passage A1 formed inside and a plurality of ventilation holes H1 communicating with the ventilation passage A1 from the surface on the upper side.

In addition, the back pad 302b has a ventilation passage A2 formed inside and a plurality of ventilation holes H2 communicating with the ventilation passage A2 from the surface on the front side. The ventilation passages A1 and A2 are open toward the seated occupant via the ventilation holes H1 and H2, respectively.

The ventilation passages A1 and A2 are connected to the blower device 80 by the duct 90. The blower device 80 is a sirocco fan disposed below the seating portion 301.

The sensor-equipped seat S5 is configured to blow out the air blown from the blower device 80 from the ventilation holes H1 and H2 toward the occupant on the seat through the duct 90 and the ventilation passages A1 and A2.

The duct 90 is formed by multi-component connection. Specifically, the duct 90 has a first duct 91, a second duct 92, a third duct 93, and a fourth duct 94.

The first duct 91 has a lower tube portion 91a extending in the front to back direction of the seat and a curved tube portion 91b extending upward while curving so as to be convex rearward from the rear end of the lower tube portion 91a. The front end portion of the lower tube portion 91a is connected to the blower device 80.

The second duct 92 is connected to the curved tube portion 91b of the first duct 91 and is provided so as to extend in the up to down direction. The second duct 92 has a flexible and stretchable first bellows portion 92a.

The third duct 93 is connected to the upper end of the second duct 92. The third duct 93 has a back connection tube portion 93a. The back connection tube portion 93a is connected to the ventilation passage A2 formed in the back pad 302b.

The fourth duct 94 is connected to the front portion of the first duct 91 and is provided so as to extend in the up to down direction. The fourth duct 94 has a flexible and stretchable second bellows portion 94a and a cushion connection tube portion 94b provided on the second bellows portion 94a. The cushion connection tube portion 94b is connected to the ventilation passage A1 formed in the cushion pad 301b.

The duct 90 is disposed so as to straddle the seating portion 301 and the backrest portion 302.

More specifically, in the duct 90, the first duct 91 and the fourth duct 94 are disposed in the seating portion 301, the third duct 93 is disposed in the backrest portion 302, and the second duct 92 is disposed so as to straddle the seating portion 301 and the backrest portion 302.

Figure 14:
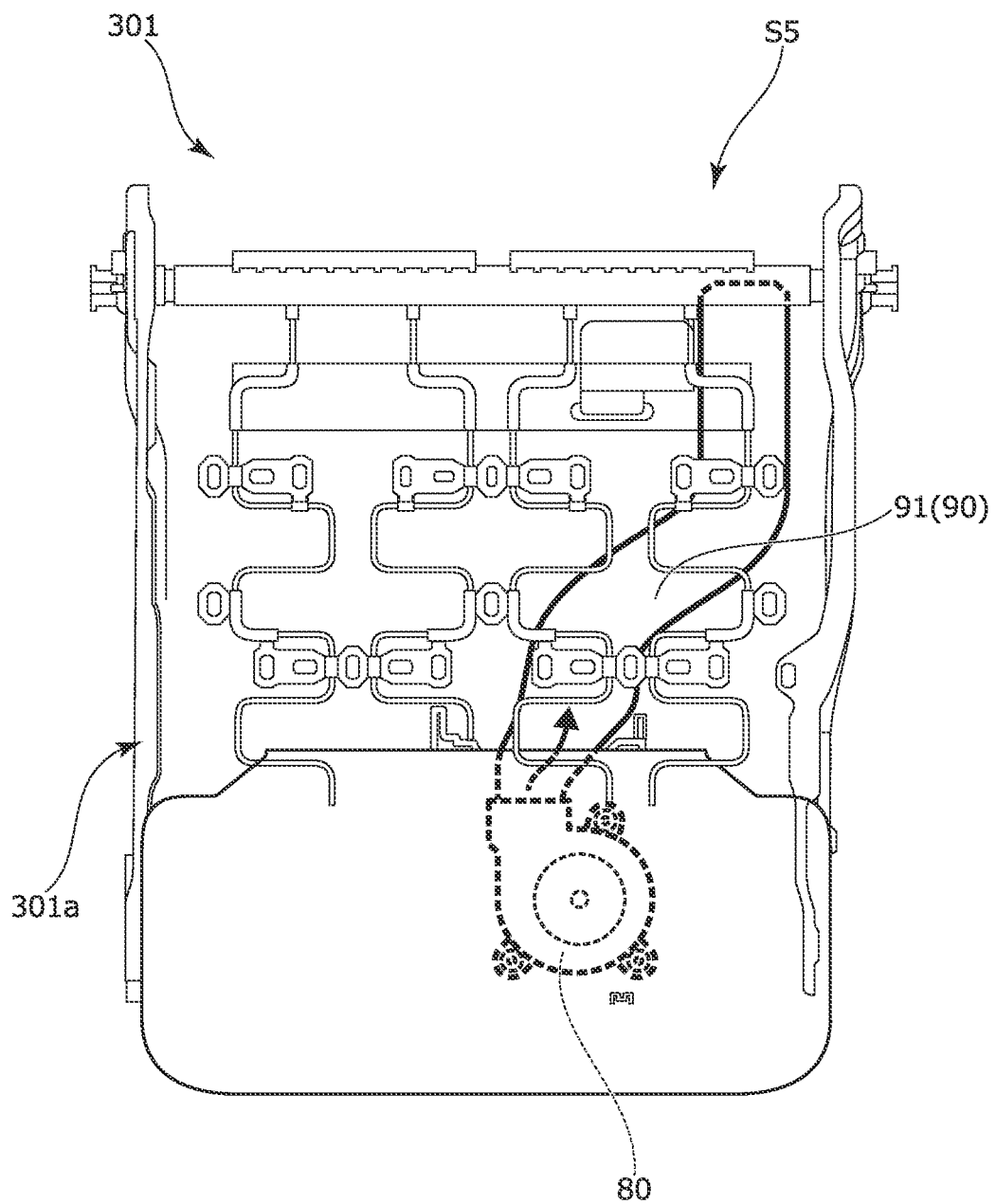
FIG. 14 is a top view illustrating the positional relationship of a seating frame, a blower device, and a duct.
Figure 15:
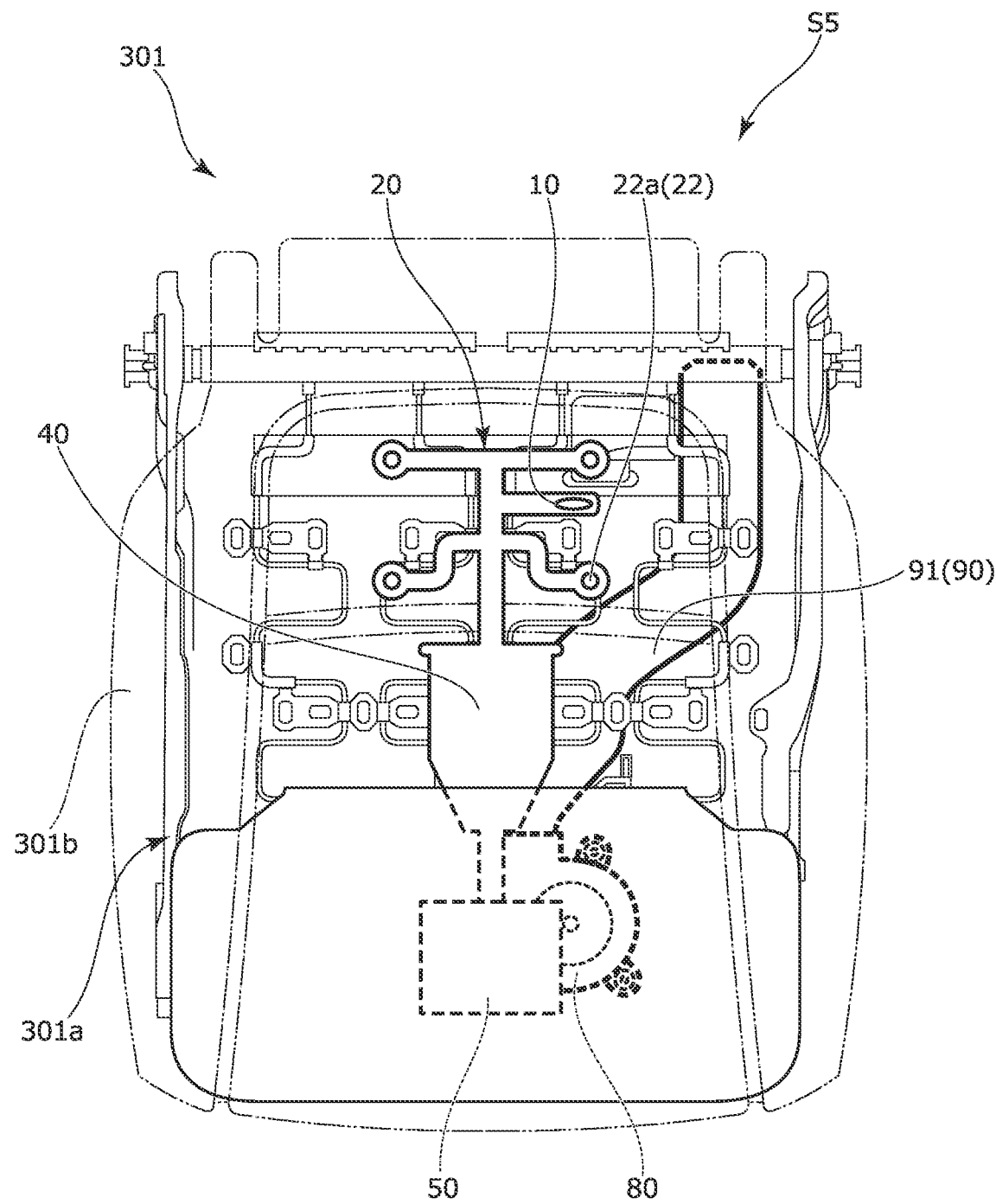
FIG. 15 is a top view illustrating the positional relationship of a wakefulness determination device, the blower device, and the duct.

As illustrated in FIGS. 13 to 15, the controller 50 has a function of controlling the blower device 80 and is provided below the seating portion 301 together with the blower device 80.

The duct 90 is disposed to the left (one side in the seat width direction) of the middle part of the seating portion 301 in the seat width direction.

The controller 50 is disposed at a position different from the position of the blower device 80 in the seat width direction and is disposed inside the blower device 80 in the seat width direction. More specifically, a part of the controller 50 is disposed at a position overlapping the blower device 80 in the seat width direction.

In addition, the controller 50 is disposed at the same position as a part of the blower device 80 in the front to back direction of the seat. More specifically, in the front to back direction of the seat, the part that includes the rear end of the controller 50 is disposed at the same position as the part that includes the front end of the blower device 80.

As illustrated in FIG. 15, in the above configuration, the first duct 91 is disposed so as to avoid the surface temperature sensor 10 and the respiration sensor 20 in a top view.

In the seat, the center position of the blower device 80 is disposed inside the outside end portion of the surface temperature sensor 10 and at least a part of the blower device 80 is disposed at a position overlapping the surface temperature sensor 10 in the front to back direction of the seat.

In addition, in the above configuration, the first duct 91 extends from the blower device 80 toward the rear of the seat as illustrated in FIG. 15. The first duct 91 is disposed at a position in front of the position overlapping the first detection unit 22a, which is the foremost detection unit 22 of the respiration sensor 20, in the up to down direction. The first duct 91 is disposed so as to bend outward in the seat width direction.

In addition, the first duct 91 is disposed so as to avoid the part of the harness 40 passing through a through hole 301e illustrated in FIG. 13 as much as possible (may be disposed so as to completely avoid the part).

With these configurations, interference between the first duct 91 and the surface temperature sensor 10, the respiration sensor 20, and the like can be avoided as much as possible.

In addition, in the above configuration, the ventilation hole H1 through which air flows and the through hole 301e are disposed at different positions (separate positions) in the front to back direction of the seat as illustrated in FIG. 15.

Then, the ventilation hole H1 and the surface temperature sensor 10 are disposed at more distant positions. Accordingly, it is possible to suppress, for example, cold air being erroneously detected by the surface temperature sensor 10.

<Sixth Embodiment of Sensor-Equipped Seat>
"Increase in Sensor Area"

Next, a sensor-equipped seat S6 according to the sixth embodiment will be described with reference to FIGS. 16 to 19.

The sensor-equipped seat S6 is different from the sensor-equipped seat S in FIG. 1 mainly in that the sensor-equipped seat S6 is a work chair including the blower device 80, the duct 90, and a sheet-shaped heart rate sensor 100 that detects a potential signal in accordance with the electrocardiographic potential of the seated occupant.

The heart rate sensor 100 detects an electrocardiographic signal that is an action potential signal entailed by the heartbeat of the seated occupant and a signal indicating the level of consciousness.

The heart rate sensor 100 includes a pair of rear electrode portions 100A and a pair of front electrode portions 100B provided in the front and rear in the seat width direction of a seating portion 401.

Figure 16:
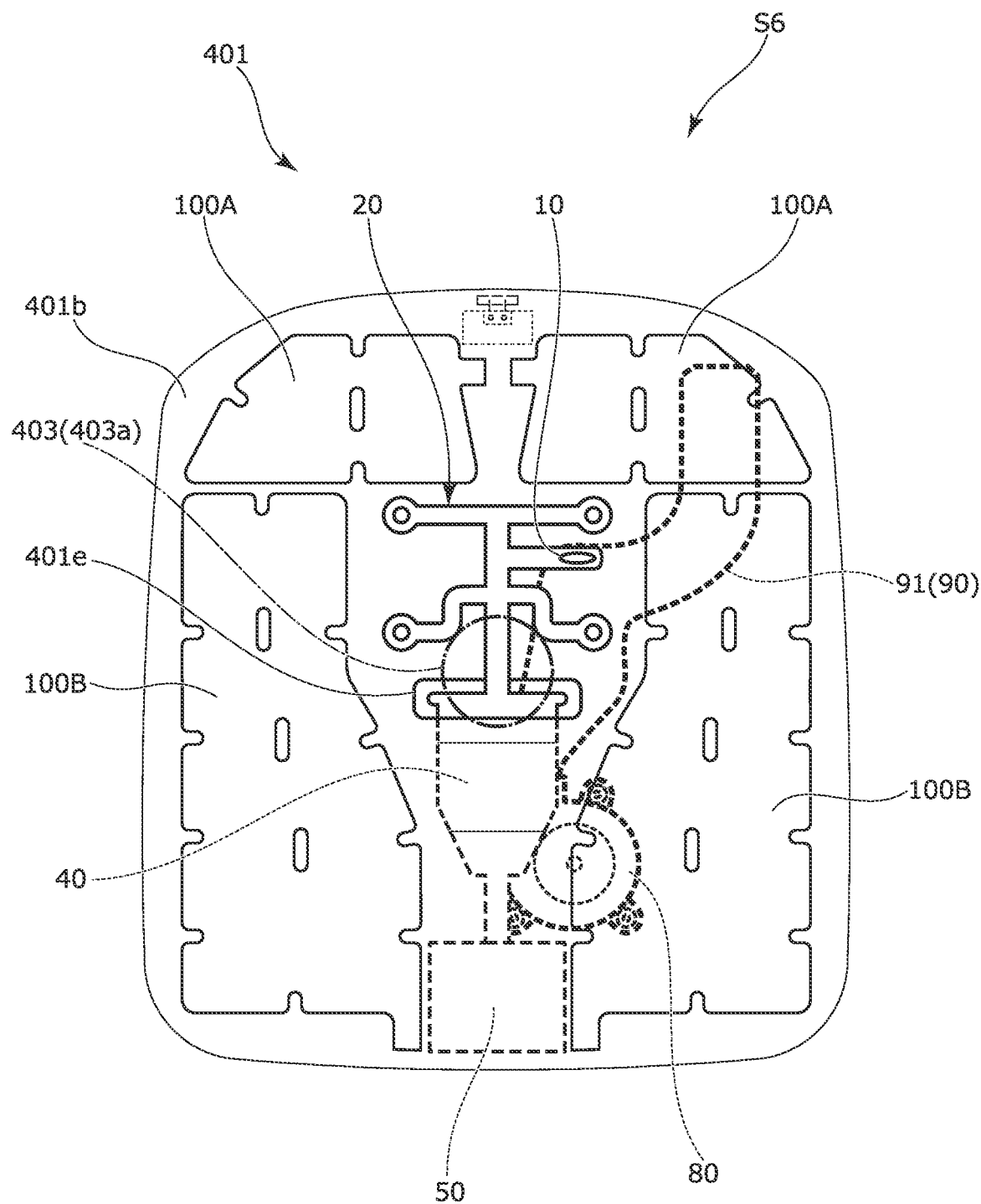
FIG. 16 is a top view illustrating the positional relationship of the wakefulness determination device, the blower device, and the duct in the sensor-equipped seat of a sixth embodiment.
Figure 18:
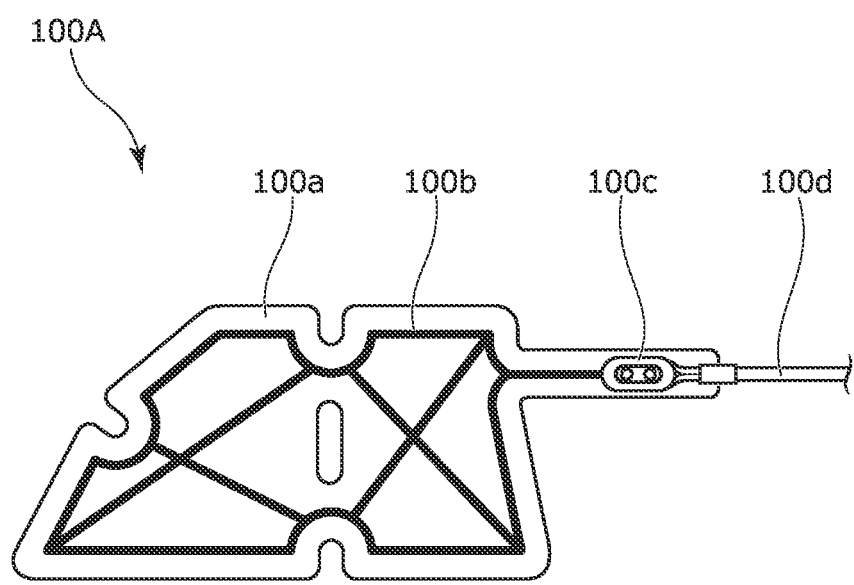
FIG. 18 is an enlarged view illustrating a rear electrode portion.
Figure 19:
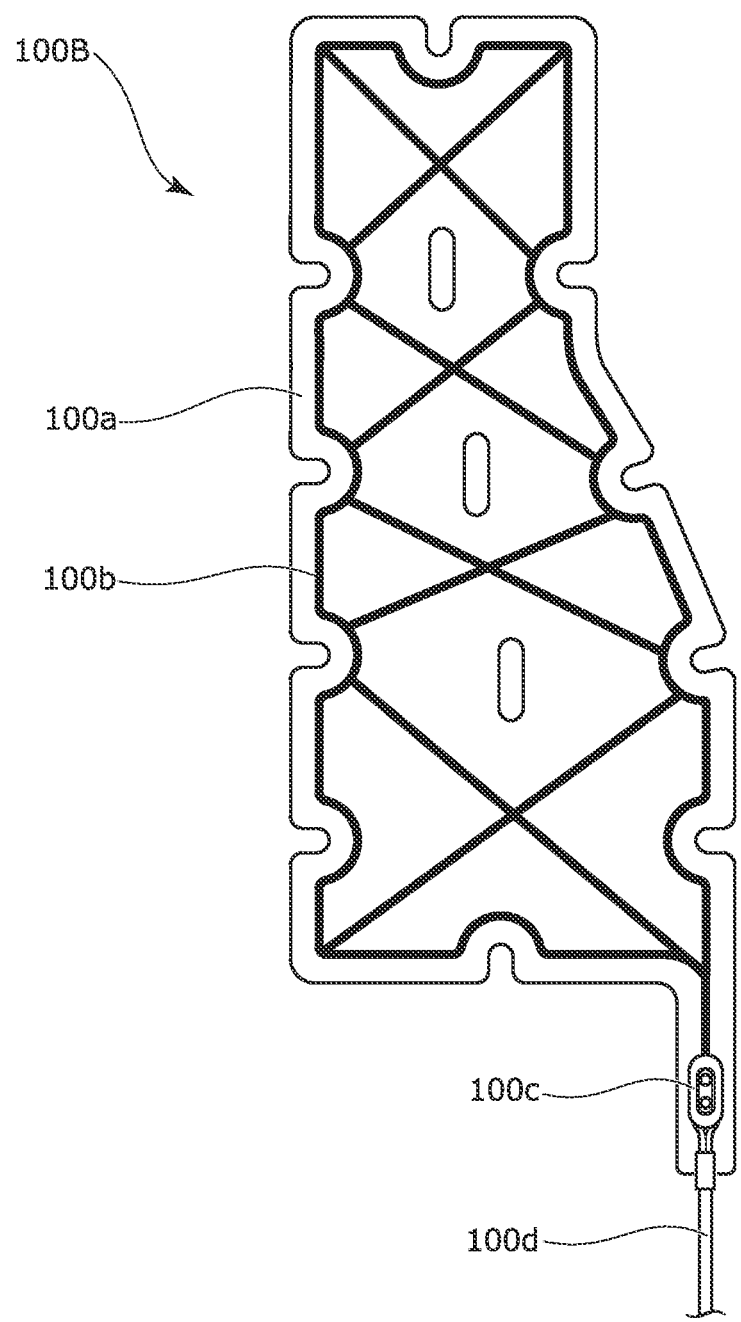
FIG. 19 is an enlarged view illustrating a front electrode portion.

As illustrated in FIGS. 16 and 18, the rear electrode portion 100A has a function of detecting the body potential of the seated occupant and is formed in a trapezoidal shape and a sheet shape.

The rear electrode portion 100A mainly includes a conductive sheet 100a and is affixed on a cushion pad 401b of the seating portion 401 by the double-faced tape affixed to the back surface of the conductive sheet 100a.

Apart of the conductive sheet 100a including a conducting wire 100b extends inward in the seat width direction, and its end portion is connected to a cable 100d by a terminal 100c.

Further, the cable 100d is connected to the controller 50.

As illustrated in FIG. 16, in the above configuration, the right and left rear electrode portions 100A are disposed so as to sandwich the respiration sensor 20 in the seat width direction. In other words, the rear electrode portion 100A is disposed together with the respiration sensor 20 at a position facing the buttocks of the seated occupant, where the stability of contact is high.

The respiratory signal of the seated occupant can be stably detected since the respiration sensor 20 is disposed at the position facing the buttocks of the seated occupant as described above. The body potential can be stably acquired since the rear electrode portion 100A is disposed.

The front electrode portion 100B functions as a ground electrode portion and acquires a potential serving as a reference potential in removing the offset signal that is included in the signal of the rear electrode portion 100A.

The front electrode portion 100B is formed in a trapezoidal shape and a sheet shape, mainly includes the conductive sheet 100a, and is affixed in the same manner as the rear electrode portion 100A.

A part of the conductive sheet 100a including the conducting wire 100b extends to the front of the seat, and its end portion is connected to the cable 100d by the terminal 100c.

The front electrode portion 100B is provided on a straight line in front of the rear electrode portion 100A and is provided at a position facing the thighs of the seated occupant.

In other words, the rear electrode portion 100A at the position facing the buttocks of the seated occupant and the front electrode portion 100B facing the thighs of the seated occupant are provided on front and rear straight lines, and thus linearly transmitted electrocardiographic signals of the same type of waveform can be detected.

By detecting the electrocardiographic signals of the same type of waveform as described above, the magnitude of the electrocardiographic signal can be detected more accurately and the physical condition of the seated occupant can be determined.

In the above configuration, the controller 50 is capable of determining the wakefulness state of the seated occupant by performing calculation for specifying the level of consciousness of the seated occupant by means of the respiratory data and the heart rate data obtained from the respiration sensor 20 and the heart rate sensor 100.

It should be noted that the controller 50 is also capable of comprehensively determining the wakefulness state of the seated occupant by acquiring the surface temperature data and the outside air temperature data obtained from the surface temperature sensor 10 and the outside air temperature sensor 30 in addition to the respiratory data and the heart rate data.

In addition, in the above configuration, a part of the duct 90 (first duct 91) is disposed so as to overlap a leg portion 403 (leg prop portion 403a) and overlap the surface temperature sensor 10 in a top view as illustrated in FIG. 16.

Accordingly, each component provided in the seating portion 401 can be disposed in a compact manner in the seat width direction.

Figure 17:
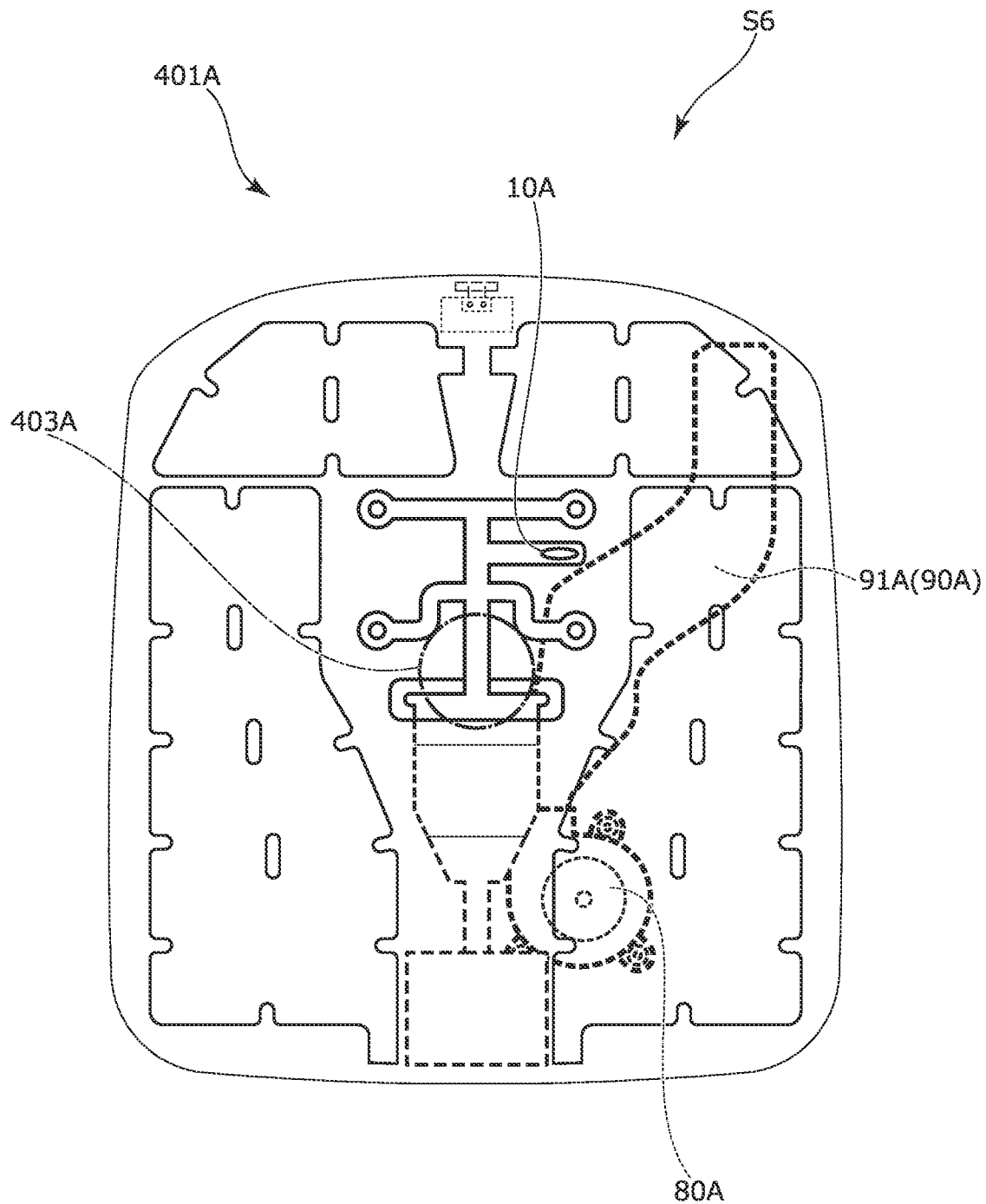
FIG. 17 is a modification example of FIG. 16.

It should be noted that a part of a duct 90A (first duct 91A) may be bent so as to avoid a leg portion 403A and avoid a surface temperature sensor 10A in a top view as illustrated in FIG. 17, which is a modification example of FIG. 16.

In this configuration, interference between the duct 90A and the leg portion 403A can be suppressed. In addition, interference between the duct 90A and the surface temperature sensor 10A can be suppressed.

In addition, in the above configuration, the center portion of the blower device 80 and the surface temperature sensor 10 are disposed so as to avoid the leg portion 403 (leg prop portion 403a) in a top view and sandwich the leg prop portion 3a in the front to back direction of the seat as illustrated in FIG. 16.

Accordingly, interference between the blower device 80 and the surface temperature sensor and the leg portion 403 can be suppressed.

In addition, in the above configuration, the duct 90 (first duct 91) is disposed at a position overlapping the surface temperature sensor 10 in a top view as illustrated in FIG. 16.

In addition, the duct 90 is disposed at a position overlapping a part of the respiration sensor 20 in a top view. More specifically, the duct 90 is disposed at a position overlapping the first detection unit 22a, which is foremost in the respiration sensor 20, in the up to down direction.

In addition, the duct 90 is disposed at a position overlapping a part of the heart rate sensor 100 in a top view. More specifically, the duct 90 is disposed at a position overlapping the left rear electrode portion 100A and the left front electrode portion 100B of the heart rate sensor 100 in the up to down direction.

<Seventh Embodiment of Sensor-Equipped Seat>
"Application to Planar Elastic Body"

Next, a sensor-equipped seat S7 according to the seventh embodiment will be described with reference to FIGS. 20 to 22.

The sensor-equipped seat S7 is different from the sensor-equipped seat S in FIG. 1 mainly in that the sensor-equipped seat S7 is a conveyance seat provided with a planar elastic body 550 in a seating portion 501 in order to improve the riding comfort of the seated occupant.

Figure 20:
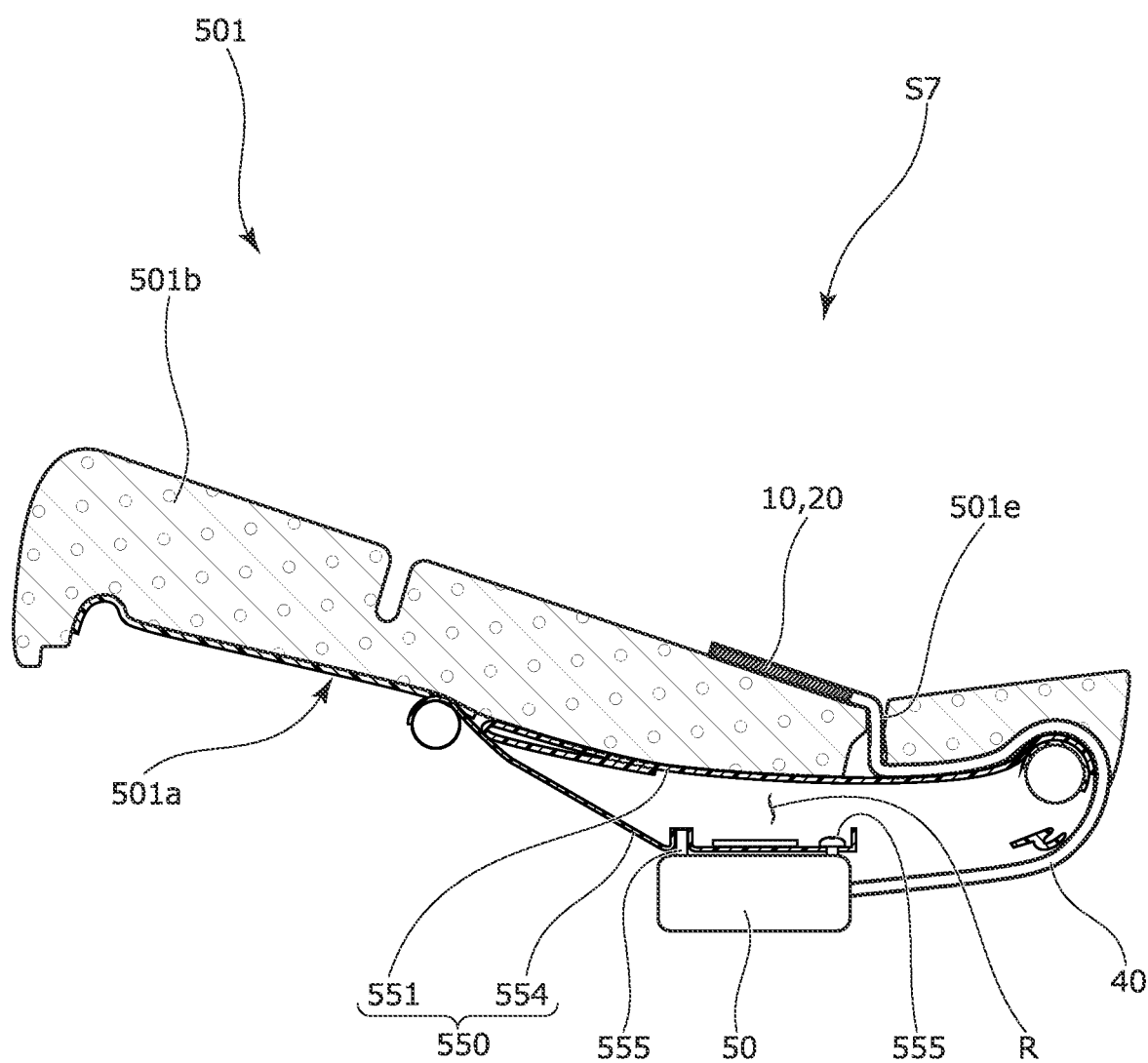
FIG. 20 is a vertical cross-sectional view of the seating portion of the sensor-equipped seat of a seventh embodiment.

As illustrated in FIG. 20, the sensor-equipped seat S7 includes the seating portion 501 and the seating portion 501 is configured by placing a cushion pad 501b on the upper surface of a seating frame 501a as a skeleton and covering the cushion pad 501b with a skin (not illustrated).

The controller 50 is attached to the bottom surface of the seating frame 501a. The surface temperature sensor 10 and the respiration sensor 20 are placed on the surface of the cushion pad 501b.

The surface temperature sensor 10 and the respiration sensor 20 are connected to the controller 50 through the harness 40.

The harness 40 extends downward from the part connected to the respiration sensor 20, passes through a through hole 501e, extends to the rear of the seat along the seating frame 501a, is folded back at the rear end part of the seating frame 501a, extends to the front of the seat, and is connected to the controller 50.

Figure 21:
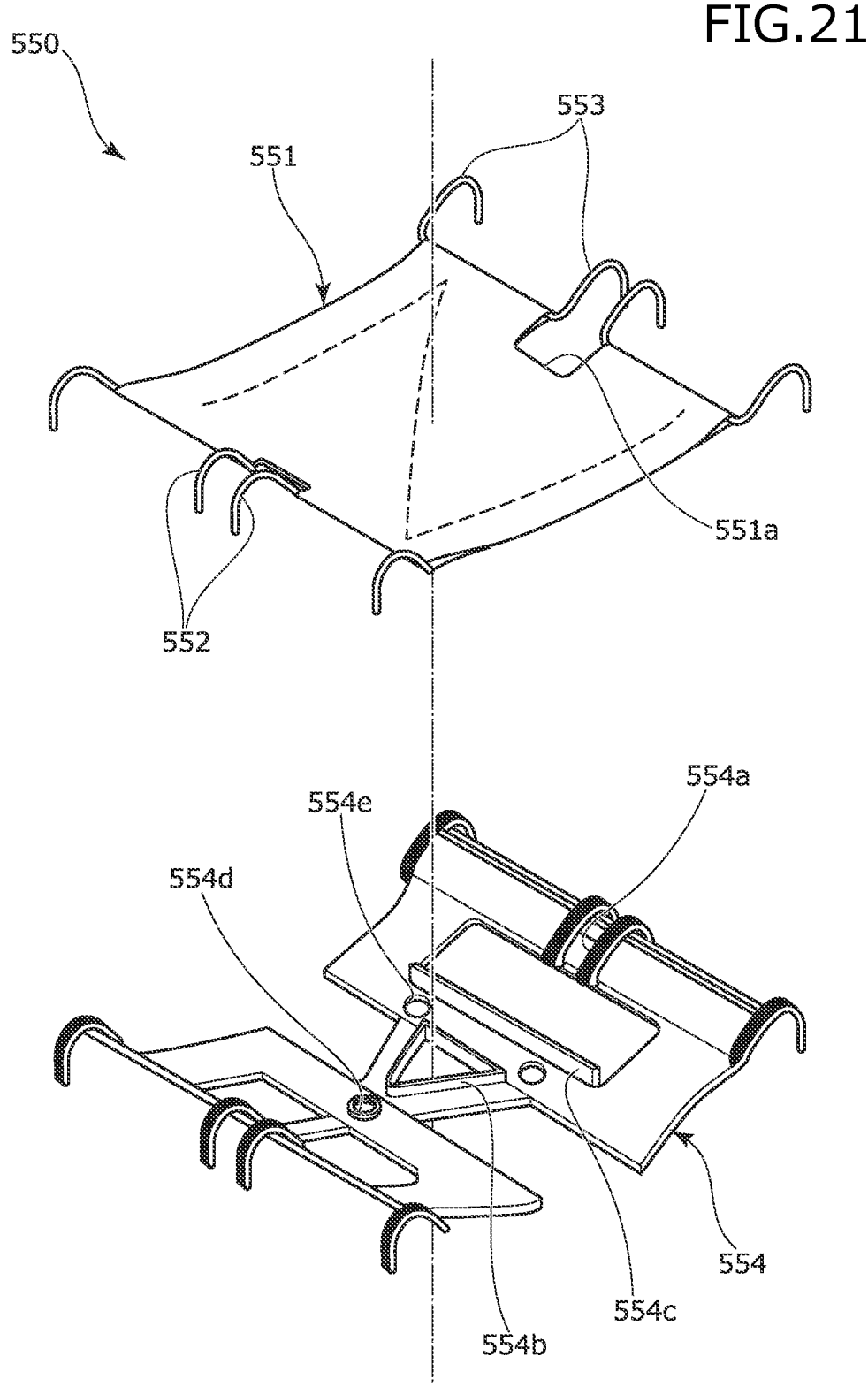
FIG. 21 is an exploded perspective view of a planar elastic body.
Figure 22:
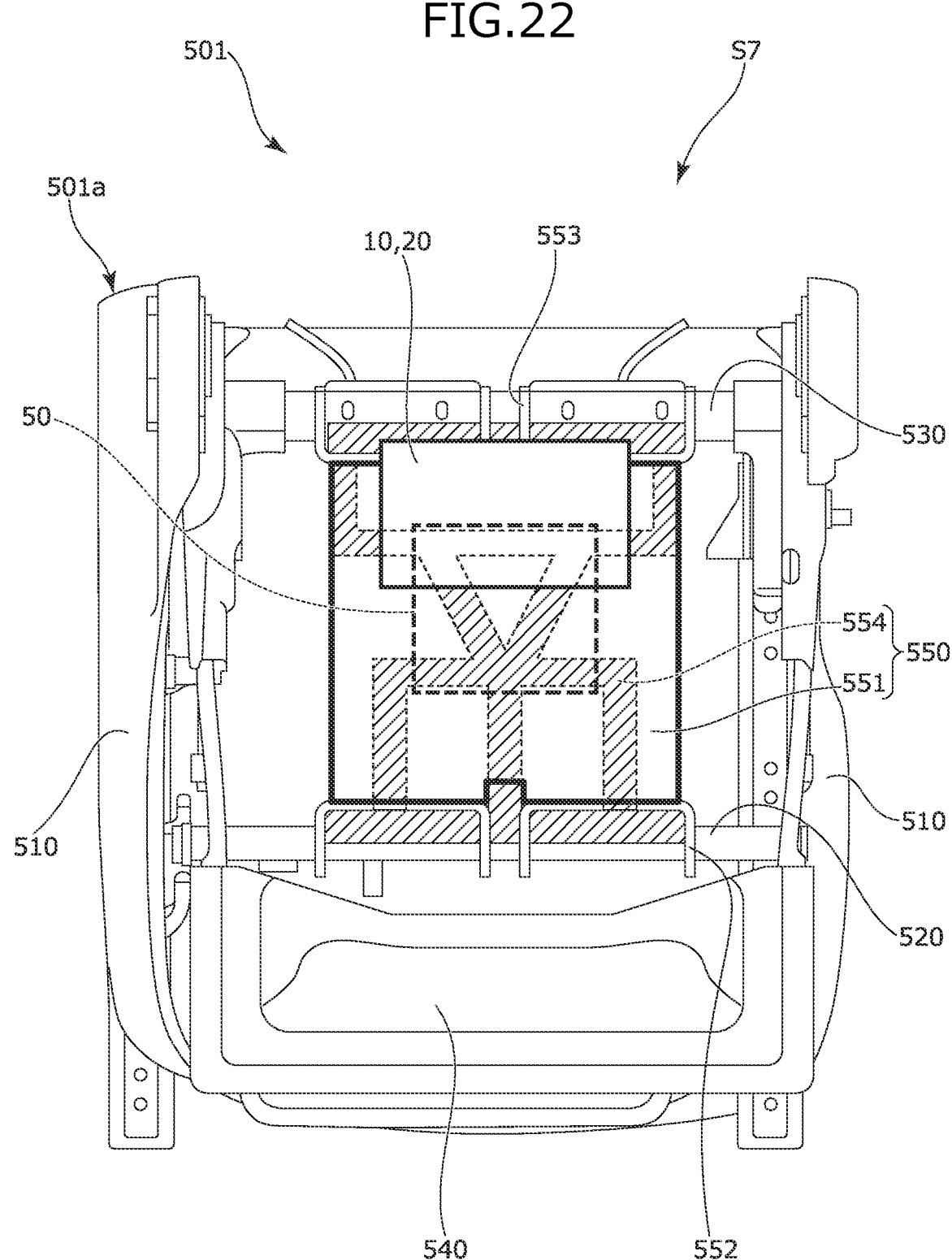
FIG. 22 is a top view illustrating the positional relationship of a respiration sensor, a controller, and the planar elastic body.

The seating frame 501a is a substantially rectangular frame-shaped body as illustrated in FIGS. 21 and 22. The seating frame 501a mainly includes right and left side frames 510 disposed on the right and left sides, a front connecting pipe 520 connecting the front end parts of the side frames 510, a rear connecting pipe 530 connecting the rear parts of the side frames 510, a plate-shaped pan frame 540 bridged between the front parts of the side frames 510, and the planar elastic body 550 bridged between the pan frame 540 and the rear connecting pipe 530.

The planar elastic body 550 mainly includes a cloth planar member 551, metallic wire members 552 and 553 respectively attached to the seat front end portion and the seat rear end portion of the planar member 551, and a resinous frame member 554 fitted to the bottom surfaces of the planar member 551 and the wire members 552 and 553.

The wire member 552 is hooked to the front connecting pipe 520, and the wire member 553 is hooked to the rear connecting pipe 530.

As illustrated in FIG. 20, when the planar member 551 and the frame member 554 are combined, a predetermined internal space R is formed between the planar member 551 and the frame member 554 in the up to down direction.

The internal space R is formed so as to widen from the front of the seat toward the rear of the seat between the planar member 551 and the frame member 554.

As illustrated in FIG. 21, in the above configuration, harness accommodating portions 551a and 554a for accommodating a part of the harness 40 are formed in the rear end portions of the planar member 551 and the frame member 554, respectively.

Accordingly, the seated occupant's discomfort can be suppressed by means of the above configuration whereas seated occupants in general are given a foreign body sensation when a thick component (such as the harness 40) is disposed on the upper surface of the planar member 551.

In addition, the harness 40 can be positioned, and thus misalignment of the harness 40 in the seat width direction can be suppressed.

As illustrated in FIG. 21, in the above configuration, a substantially triangular reinforcement rib 554b and a substantially rectangular plate-shaped second reinforcement rib 554c for frame member rigidity enhancement are formed at the middle part of the frame member 554.

In addition, controller attachment portions 554d and 554e for attaching the controller 50 are formed at the parts of the frame member 554 where the reinforcement rib 554b and the second reinforcement rib 554c are formed.

The controller attachment portion 554e in particular is disposed between the reinforcement rib 554b and the second reinforcement rib 554c in the front to back direction of the seat, and these components are lined up in the front to back direction of the seat.

Accordingly, the rigidity of assembly can be enhanced in assembling the controller 50 on the bottom surface of the frame member 554 by means of an attachment bolt 555.

In addition, the reinforcement rib 554b and the second reinforcement rib 554c are formed at the middle part of the frame member 554, and thus foreign matter intrusion can be suppressed at the middle part.

In addition, in the above configuration, the attachment bolt 555 is disposed at a relatively wide space part of the internal space R, which is formed between the planar member 551 and the frame member 554, as illustrated in FIG. 20.

Accordingly, the attachment workability of the attachment bolt 555 can be improved.

In addition, in the above configuration, the respiration sensor 20 is disposed not on the front side of the seat but on the rear side of the seat and the controller 50 is disposed on the bottom surface of the planar elastic body 550 on the rear side of the seat as illustrated in FIG. 20.

More specifically, the respiration sensor 20 and the controller 50 are disposed at positions overlapping each other in the up to down direction.

Accordingly, the total length of the harness 40 connecting the respiration sensor 20 and the controller 50 can be reduced and the wakefulness determination device can be compact.

In addition, in the above configuration, the harness 40 (linear member 40) is disposed at the rear part of the cushion pad 501b and avoids the middle part of the cushion pad 501b, where a seating load is likely to be applied from the seated occupant, as illustrated in FIG. 20.

Accordingly, the seated occupant is unlikely to feel the thickness of the harness 40 and deterioration of the seating feeling can be suppressed.

In addition, the harness 40 extends to the rear of the seat and avoids the planar elastic body 550, and thus there is no need to separately form a harness through hole in the planar elastic body 550 (planar member 551) and deterioration of seating feeling can be suppressed.

Further, the harness 40 extends to the rear of the seat, and thus seating load application to the harness 40 can be suppressed.

It should be noted that the harness 40 (linear member 40) connects the surface temperature and respiration sensors 10 and 20 and the controller 50 and, if the sensor-equipped seat S7 separately includes the heart rate sensor 100 illustrated in FIG. 16, it is preferable that the harness 40 (linear member 40) connects the heart rate sensor 100 as well.

OTHER EMBODIMENTS

As illustrated in FIG. 1, in the above embodiment, the sensor-equipped seat S includes the wakefulness determination device D detecting the seated occupant-side seat surface temperature (body surface temperature of the seated occupant), the seat body outside temperature, and the respiration of the seated occupant and determining the wakefulness state of the seated occupant by calculating the parameters. However, the present invention can be changed without any particular limitation.

Specifically, the sensor-equipped seat S may include a physical condition change determination device instead and the physical condition change determination device may detect the body surface temperature of the seated occupant, the seat body outside temperature, and the respiration of the seated occupant and determine a change in physical condition other than the wakefulness state of the seated occupant.

In addition, the sensor-equipped seat may include a physical condition change determination device detecting non-respiratory biological information in addition to the seat surface temperature and the outside temperature and determining a change in the physical condition of the seated occupant. Examples of the non-respiratory biological information include electrocardiogram, blood pressure, and heartbeat.

As illustrated in FIG. 1, in the above embodiment, the surface temperature sensor 10, the respiration sensor 20, and the outside air temperature sensor 30 are attached in the seating portion 1. However, the present invention is not particularly limited thereto and the sensors 10, 20, and 30 may be attached in the backrest portion 2.

As illustrated in FIG. 2, in the above embodiment, the harness 40A is formed by bundling the transmission paths of the surface temperature sensor 10 and the respiration sensor 20 and connects the sensors 10 and 20 and the controller 50. However, the present invention is not particularly limited thereto and the first harness 40A for the surface temperature sensor 10 and the second harness 40A for the respiration sensor 20 may be separated from each other.

Even in that case, it is desirable that both the first harness 40A and the second harness 40A extend through the through holes 1d and 1e and a compact disposition can be realized.

In the above embodiments, a work chair and a vehicle seat for use in automobiles have been described as specific examples. However, the present invention is not limited thereto and can be used as a conveyance seat for airplanes, ships, and so on as well as a vehicle seat for trains, buses, and so on.

The work chair and the vehicle seat according to the present invention have been mainly described in the present embodiments.

However, the above-described embodiments are merely examples for facilitating the understanding of the present invention and do not limit the present invention. The present invention can be modified and improved without departing from the spirit thereof, and it is a matter of course that the present invention includes equivalents thereof.

In particular, the disposition and configuration of the surface temperature sensor, the outside air temperature sensor, and the respiration sensor described in the above embodiments are merely examples and do not limit the present invention.

REFERENCE SIGNS LIST

S, S2, S3, S4, S5, S6, S7: sensor-equipped seat
1, 101, 201, 301, 401, 401A, 501: seating portion
 1a, 201a, 301a, 501a: seating frame
 1b, 101b, 201b, 301b, 401b, 501b: pad (cushion pad)
 1c, 101c: skin
 1d, 1e, 101f, 201d, 201e, 301e, 401e, 501e: through hole
 201f, 201g, 201h: hanging recess portion
2, 302: backrest portion
 302b: back pad
3, 403, 403A: leg portion 3a, 403a: leg prop portion
3b: leg branching portion
D: wakefulness determination device (biological information measuring device)
10, 10A: surface temperature sensor
11, 21: seat base material
12, 22: detection unit
  22a: first detection unit
  22b: second detection unit
13, 23: transmission path
14, 24: connection path
20: respiration sensor
30: outside air temperature sensor
40: harness (linear member)
  40A, 40B: harness
50: controller
  50a: recording unit
  50b: waveform generation unit
  50c: first calculation unit
  50d: second calculation unit
  50e: wakefulness determination unit (determination unit)
  50f: drive execution unit
51: drive unit
  51a: drive motor
  51b: attachment member
52: battery
  52a: attachment member
60: protective cover
70: seat heater
71: seat base material
72: heater wire
73: connector
80, 80A: blower device
90, 90A: duct
91, 91A: first duct
  91a: lower tube portion
  91b: curved tube portion
92: second duct
  92a: first bellows portion
93: third duct
  93a: back connection tube portion
94: fourth duct
  94a: second bellows portion
  94b: cushion connection tube portion
A1, A2: ventilation passage
H1, H2: ventilation hole
100: heart rate sensor
  100A: rear electrode portion
  100B: front electrode portion
    100a: conductive sheet
    100b: conducting wire
    100c: terminal
    100d: cable
510: side frame
520: front connecting pipe
530: rear connecting pipe
540: pan frame
550: planar elastic body
551: planar member
  551a: harness accommodating portion
552, 553: wire member
554: frame member
  554a: harness accommodating portion
  554b: reinforcement rib
  554c: second reinforcement rib
  554d, 554e: controller attachment portion
555: attachment bolt
R: internal space

The invention claimed is:

1. A sensor-equipped seat comprising:
a surface temperature sensor detecting a seat surface temperature on a seated occupant side in a seat body and acquiring surface temperature data fluctuating with the seat surface temperature;
an outside air temperature sensor detecting a temperature outside the seat body and acquiring outside air temperature data fluctuating with the outside temperature; and
a controller having a calculation unit calculating the surface temperature data and the outside air temperature data and a determination unit determining a change in physical condition of the seated occupant on the basis of information calculated by the calculation unit,
wherein the calculation unit calculates, by computation, a degree of change in temperature difference from the seat surface temperature in the surface temperature data and the outside air temperature in the outside air temperature data, the degree of change in temperature difference being a degree of change per unit time, and
the determination unit is a wakefulness determination unit determining a wakefulness state of the seated occupant on the basis of the degree of change in temperature difference calculated by the calculation unit.

2. The sensor-equipped seat according to claim 1, wherein the seat body is provided with a seating portion supporting the seated occupant from below, and
the surface temperature sensor is attached to the seating portion.

3. The sensor-equipped seat according to claim 2, wherein the surface temperature sensor is attached at a part behind a middle portion of the seating portion in a front to back direction of the seat.

4. The sensor-equipped seat according to claim 2, wherein the seating portion has a pad formed of a cushion material,
the surface temperature sensor is provided on a surface side of the pad,
the controller is provided on a back surface side of the pad, and
a harness connecting the surface temperature sensor and the controller through a through hole formed in the pad is provided.

5. The sensor-equipped seat according to claim 4, wherein
a recess portion recessed in a thickness direction of the pad is formed at a position different from a position of the through hole in the surface of the pad, and
the surface temperature sensor is disposed in the recess portion.

6. The sensor-equipped seat according to claim 4, comprising a respiration sensor attached to the seating portion and having a detection unit detecting a respiratory signal of the seated occupant, wherein
the detection unit has a first detection unit and a second detection unit disposed at different positions in a front to back direction of the seat, and
the surface temperature sensor is disposed between the first detection unit and the second detection unit.

7. The sensor-equipped seat according to claim 6, wherein the respiration sensor is provided on the surface side of the pad, and
a second harness connecting the respiration sensor and the controller through the through hole formed in the pad is provided.

8. The sensor-equipped seat according to claim 6, wherein
the respiration sensor detects the respiratory signal of the seated occupant and acquires respiratory data fluctuating with respiration,
the controller further has a second calculation unit calculating, by computation, a degree of change in respiration, the degree of change in respiration being a degree of change in the respiratory data per unit time, and
the wakefulness determination unit determines the wakefulness state of the seated occupant by using a Bayesian filter in which a probability of the seated occupant's drowsiness with regard to the degree of change in respiration is set as a likelihood and the likelihood is multiplied by a prior probability of drowsiness.

9. The sensor-equipped seat according to claim 2, wherein
the seating portion is configured by covering a pad as a cushion material with a skin,
a seat heater attached to a back surface side of the skin is provided between the skin and the pad in the seating portion, and
the seat heater is disposed on a surface of the pad at a position different from a position of the surface temperature sensor.

* * * * *